(12) United States Patent
Yang et al.

(10) Patent No.: US 7,560,267 B2
(45) Date of Patent: Jul. 14, 2009

(54) APPARATUS AND METHODS FOR ON-CHIP MONITORING OF CELLULAR REACTIONS

(75) Inventors: Mengsu Yang, Kowloon (HK); Cheuk Wing Li, Chai Wan (HK); Jun Yang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 1059 days.

(21) Appl. No.: 10/100,276

(22) Filed: Mar. 18, 2002

(65) Prior Publication Data

US 2003/0175944 A1 Sep. 18, 2003

(51) Int. Cl.
C12M 1/00 (2006.01)
C12M 3/00 (2006.01)
G01N 33/00 (2006.01)
G01N 15/06 (2006.01)
A61K 39/02 (2006.01)

(52) U.S. Cl. ............... 435/283.1; 435/308.1; 422/68.1; 422/243

(58) Field of Classification Search .................. 436/43, 436/52, 174, 180; 422/81, 100, 129, 68.1, 422/243; 209/105; 435/283.1, 308.1
See application file for complete search history.

(56) References Cited

U.S. PATENT DOCUMENTS

| | | | | |
|---|---|---|---|---|
| 5,922,210 A | * | 7/1999 | Brody et al. | 210/767 |
| 5,948,684 A | | 9/1999 | Weigl et al. | 436/52 |
| 5,971,158 A | * | 10/1999 | Yager et al. | 209/155 |
| 5,972,710 A | * | 10/1999 | Weigl et al. | 436/34 |
| 6,171,865 B1 | | 1/2001 | Weigl et al. | 436/52 |
| 6,193,647 B1 | | 2/2001 | Beebe et al. | 600/33 |
| 6,200,814 B1 | * | 3/2001 | Malmqvist et al. | 436/52 |
| 6,632,619 B1 | * | 10/2003 | Harrison et al. | 435/7.2 |
| 6,632,655 B1 | * | 10/2003 | Mehta et al. | 506/14 |

OTHER PUBLICATIONS

Yang et al. (Yang) "Cell Docking and On-Chip Monitoring of Cellular Reactions with a Controlled Concentration Gradient on a Microfuidic Device," Analytical Chemistry, 74: 3991-4001 (2002).*
The Random House Dictionary 224 (1982).*
Oleschuk et al., "Trapping of Bead-Based Reagents within Microfluidic Systems: On-Chip Solid-Phase Extraction and Electrochromatography," Anal. Chem. 2000, 72, 585-590.
Austin et al., "Micro and Nanopore Structures For Biological Applications," Transducers '97, 1997 International Conference on Solid-State Sensors and Actuators, Chicago, Jun. 16-19, 1997, 1303-1305.

(Continued)

*Primary Examiner*—Sue Liu
(74) *Attorney, Agent, or Firm*—Heslin Rothenberg Farley & Mesiti P.C.

(57) ABSTRACT

This invention relates to apparatus and methods for on-chip monitoring of cellular reactions, and in particular to such an apparatus and method that enables soft-docking of cells by using a dam wall that is parallel to the direction of fluid flow. The invention further relates to an apparatus and method capable of generating a controlled concentration gradient, and in particular a concentration gradient such that the cells are aligned in the direction of the concentration gradient after docking.

5 Claims, 19 Drawing Sheets

OTHER PUBLICATIONS

Muller et al., "A 3-D microelectrode system for handling and caging single cells and particles," Biosensors & Bioelectronics 14: 247-256 1999.

Dertinger et al., "Generation of Gradients Having Complex Shapes Using Microfluidic Networks," Anal. Chem. 73: 1240-1246 2001.

Jacobson et al., "Microfluidic Devices for Electrokinetically Driven Parallel and Serial Mixing," Anal. Chem. 71: 4455-4459 1999.

Kamholz et al., "Quantitative Analysis of Molecular Interaction in a Microfluidic Channel: The T-Sensor," Anal. Chem. 71: 5340-5347 1999.

Mitchell et al., "Towards Organic Synthesis in Microfluidic Devices: Multicomponent Reactions For the Construction of Compound Libraries," A. van den Berg et al. (eds.), Micro Total Analysis Systems 463-465 2000.

Delamarche et al., "Microfluidic Networks for Chemical Patterning of Substrates: Design and Application to Bioassays," J. Am. Chem. Soc. 120: 500-508 1998.

Lin et al., "Rapid Measurements of Intracelluar Calcium Using a Fluorescence Plate Reader," BioTechniques 26: 318-326 Feb. 1999.

Thomas et al., "A comparison of fluorescent Ca2+ indicator properties and their use in measuring elementary and global Ca2+ signals," Cell Calcium 28(4) 213-223 2000.

Hubley et al., "The effects of temperature, pH, and magnesium on the diffusion coefficient of ATP in solutions of physiological ionic strength," Biochimica et Biophysica Acta 1291: 115-121 1996.

Herbert et al., "Micropatterning gradients and controlling surface densities of photoactivatable biomolecules on self-assembled monolayers of oligo(ethylene glycol) alkanethiolates," Chemistry & Biology 4 (10):731-737 1997.

Jeon et al., "Generation of Solution and Surface Gradients Using Microfluidic Systems," Langmuir 16: 8311-8316 2000.

Hediger et al., "Fabrication of a novel microsystem for the electrical characterisation of cell arrays," Sensors and Actuators B 56: 175-180 1999.

Hediger et al., "Biosystem for the culture and characterisation of epithelial cell tissues," Sensors and Actuators B 63: 63-73 2000.

Takayama et al., "Patterning cells and their environments using multiple laminar fluid flows in capillary networks," Proc. Natl Acad. Sci. USA, 96: 5545-5548 May 1999.

Li et al., "Transport, Manipulation, and Reaction of Biological Cells On-Chip Using Electrokinetic Effects," Anal. Chem. 69: 1564-1568 1997.

Liedberg et al., Molecular Gradients of omega-Substituted Alkanethiols on Gold: Preparation and Characterization, Langmuir 11: 3821-3827 1995.

Darling et al., "Integration of Microelectrodes With Etched Microchannels For In-Stream Electrochemical Analysis," A. van den Berg et al. (eds.), Micro Total Analysis Systems 105-108 2000.

Glasgow et al., "Individual Embryo Transport and Retention On A Chip," A. van den Berg et al. (eds.), Micro Total Analysis Systems 199-202 2000.

Jensen, "Smaller, faster chemistry," Nature 393: 735-737 Jun. 25, 1998.

Darling et al., "Integration of Microelectrodes With Etched Microchannels for In-Stream Electrochemical Analysis," A. van den Berg et al. (eds), Micro Total Analysis Systems, '98, pp. 105-108, 1998.

Glasgow et al., "Individual Embryo Transport and Retention On A Chip," A. van den Berg et al., (eds.), Micro Total Analysis Systems '98, pp. 199-202, 1998.

* cited by examiner

A

B

APPARATUS AND METHODS FOR ON-CHIP MONITORING OF CELLULAR REACTIONS

FIELD OF THE INVENTION

This invention relates to apparatus and methods for on-chip monitoring of cellular reactions, and in particular to such an apparatus and method that enables soft-docking of cells. The invention further relates to an apparatus and method capable of generating a controlled concentration gradient, and in particular a concentration gradient such that the cells are aligned in the direction of the concentration gradient after docking.

BACKGROUND OF THE INVENTION

The generation of a concentration gradient is very important in many biological and chemical research processes, and analyte concentration is an important parameter in every chemical or biochemical reaction. Taking cytotoxicity assay as an example, a drug will exhibit efficacy at an optimal concentration but may be toxic at high concentrations. To evaluate the optimal dosage, serial dilution is a simple and common approach. Usually many individual experiments with descending concentrations are performed where the optimal concentration will lie within a concentration range. The more individual dilution experiments that are performed, the closer the range and the more accurate the result.

On-chip monitoring of cell reactions has great potential for automating such experiments and enabling large numbers of experiments to be performed easily and repeatedly. However, on-chip monitoring poses a number of technical challenges including the issues of cell manipulation and the generation of a concentration gradient.

Concerning cell manipulation, there have been a number of previous proposals for manipulating biological cells on a microfluidic device. These include electrokinetic transport techniques, entrapment of a cell by a constriction structure, the use of weirs, capturing cells by grid, negative dielectrophoresis (nDEP) traps, and cages for single eukaryotic cells.

To avoid mammalian cell distortion, gentle fluid manipulation is required, such as the technique of negative dielectrophoresis (nDEP). In nDEP, cells are levitated and contact-free in solution. Depending on the electrode array structure, funnel, aligner, cage and switch modules can be performed and controlled by AC current. However, efficient particle trapping requires very low flow rate (micro liters/hr). In addition, the fabrication and alignment of three-dimensional microelectrode systems are also complicated. Single cell manipulation is possible, however, where an embryonic cell was trapped by shallow constriction with less complicated channel geometry.

Dilution in micro-devices involves joining analyte and buffer streams followed by diffusive mixing. In some of the dilution models, rapid equilibrium is achieved by repeatedly split, mixed and recombined streams of fluorophore and buffer. Other devices examine concentration gradient in short straight channel before analytes were equilibrated within channel.

SUMMARY OF THE INVENTION

According to the present invention there is provided apparatus for on-chip monitoring of cellular reactions comprising, a surface formed with a plurality of channels for fluid flow and means for supplying a cell bearing fluid to a first of said channels, wherein a second of said channels extends parallel to the first said channel for at least a part of their length and wherein the first and second channels are separated over said at least one part of their length by a wall defining a dam and over which fluid may flow from the first of said channels into the second of said two channels.

Viewed from another aspect the present invention provides apparatus for on-chip monitoring of cellular reactions comprising, means for immobilising a plurality of viable cells in a line extending in a first direction, means for supplying a reagent to said cells, and means for forming a concentration gradient of said reagent along said line.

Viewed from a still further aspect the invention provides apparatus for generating a concentration gradient of a reagent supplied to a device for on-chip monitoring of a cellular reaction, comprising a first channel for receiving said reagent, a second channel adjacent said first channel and said first and second channels being in fluid communication, at least one further channel for supplying a diluting fluid to said first channel, and means for selectively either supplying or not supplying a buffer solution to said second channel whereby said apparatus may operate in two dilution modes dependent on whether or not said buffer solution is supplied to said second channel.

The present invention also extends to a method for on-chip monitoring of cellular reactions comprising, immobilising a plurality of viable cells in a line extending in a first direction, supplying a reagent to said cells, and forming a concentration gradient of said reagent along said line.

Further, in another aspect the invention relates to a method for immobilising cells in an apparatus for on-chip monitoring of cellular reactions comprising, providing said apparatus with first and second fluid channels formed for at least a part of their length parallel to each other and divided from each other in said at least part of their length by a wall defining a dam over which fluid may flow, supplying a cell bearing fluid to a first channel at a first liquid pressure, and supplying a liquid to said second channel at a second liquid pressure that is lower than said first liquid pressure.

In a further aspect, the present invention provides a method for generating a concentration gradient of a reagent supplied to an apparatus for on-chip monitoring of cellular reactions comprising, supplying said reagent to a first channel, selectively supplying a buffer to a second channel adjacent said first channel and in fluid communication therewith, and supplying a diluting agent to said first channel at a dilution intersection.

BRIEF DESCRIPTION OF THE DRAWINGS

Some embodiments of the invention will now be described by way of example and with reference to the accompanying drawings, in which.

DETAILED DESCRIPTION OF PREFERRED EMBODIMENT

Figure 1:
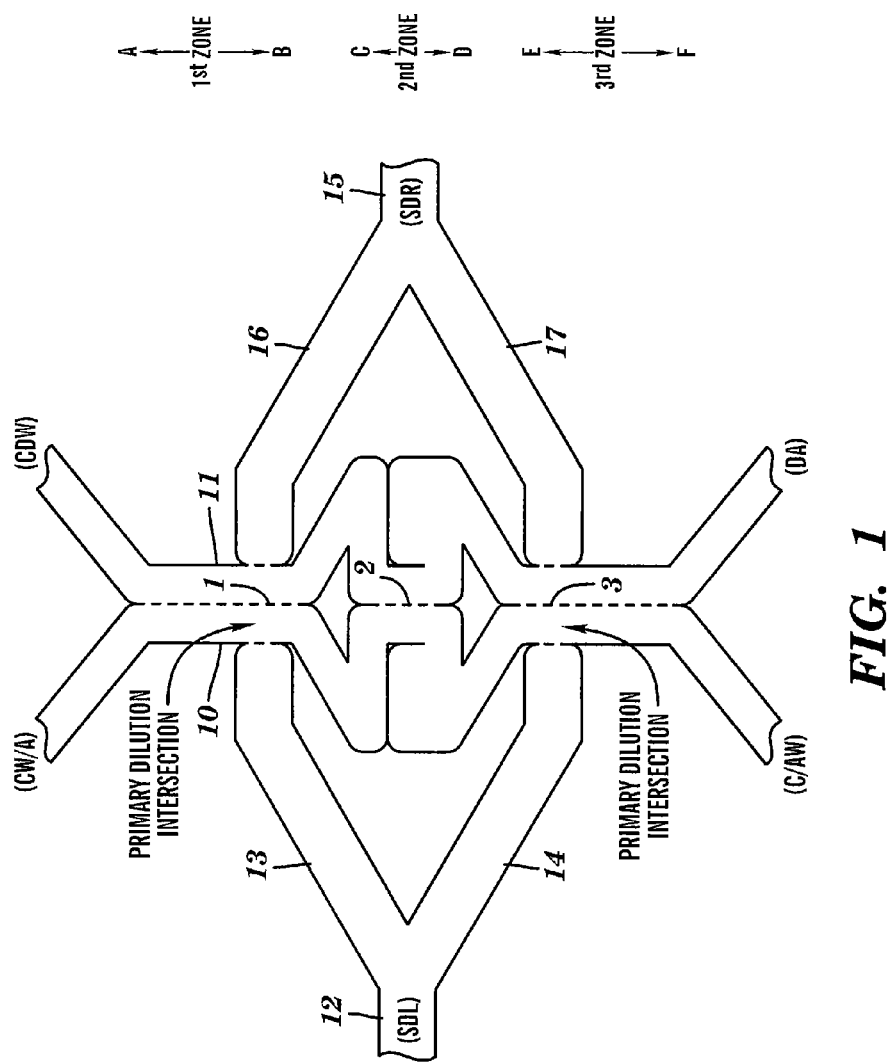
FIG. 1 is a schematic view of the apparatus of an embodiment of the invention.

FIG. 1 illustrates the microchannels formed as part of a first embodiment of the invention. The apparatus comprises a quartz plate on which the channels are formed by a traditional photolithography method followed by HF etching. The channels are etched to a depth of about 18 μm. Following formation of the channels, the quartz plate was covered by a cover formed of poly(dimethylsiloxane) (PDMS) prepared in 10:1 silicone elastomer with curing agent (Sylgard 184, Dow Corning, Midland, Mich.) and cured according to the published protocol.

In the apparatus of FIG. 1, the apparatus is formed with six inlets/outlets which connect to vials (not shown) indicated by the acronyms CW/A (cell waste/analyte), CDW (complex dilution waste), SDL (serial dilution left), SDR (serial dilution right), C/AW (cell/analyte waste) and DA (docking attenuator). The functions of these inlets/outlets and the associated vials will become clear from the following description of firstly the manner of cell docking, and then secondly the generation of a concentration gradient.

It should also be noted in FIG. 1 that broken lines 1,2 and 3 indicate dam walls that divide two channels but which are formed such that they do not extend to the full height of the channels whereby fluid may flow over the dam walls from one channel and into another adjacent channel. It is important to note that the dam walls are parallel to the direction of fluid flow in the channels. Fragile mammalian cells will experience distortion when stopped at traditional dam structures constructed perpendicular to flow route, but by constructing a dam along the major flow route, so that the dam wall is parallel to the principal direction of fluid flow, cells may be aligned and immobilized with high viability.

Figure 4:
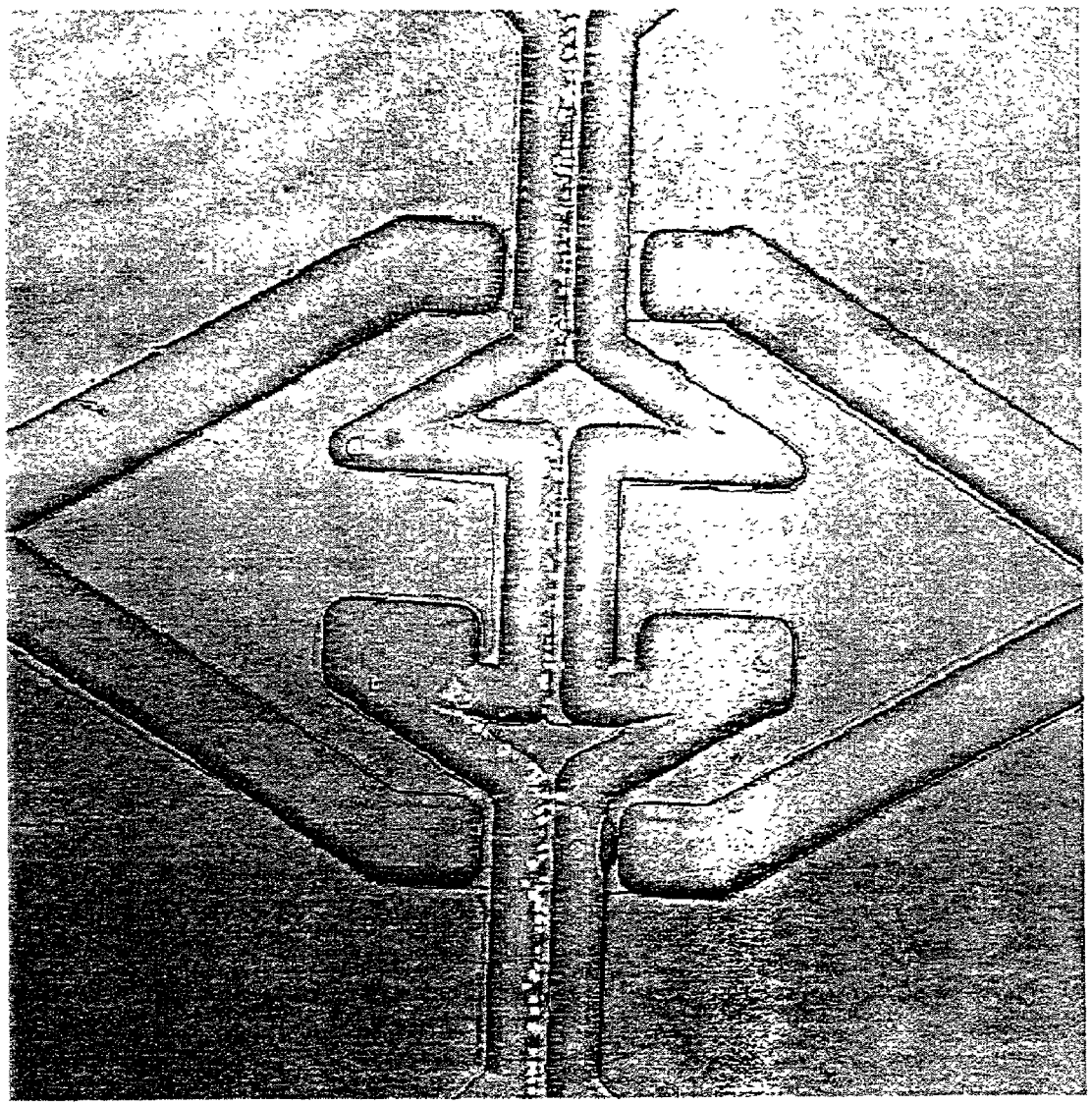
FIG. 4 shows a column of cells docked by an embodiment of the invention, FIG. 5 plots concentration gradient profiles generated by simple and complex modes, FIG. 6 are confocal images of ATP-dependent calcium uptake reactions as monitored using an embodiment of the present invention, FIG. 7 are plots of the relative cellular fluorescence of the cells of FIG. 6.

This mechanism is illustrated in FIGS. 2(a) & (b). The dam allows liquid to pass over but cells are trapped (docked) along the dam while the flow will be attenuated after cell docking. Liquid pressure will not increase significantly on cells, as the fluid flows along the major route. Only cells running closer to channel wall (laminas of slower velocities) will be driven by the small pressure difference and docked gently. Other cells are driven away towards the waste vial (CW/A). To improve the docking performance a small quantity of flow is allowed to come from vial Y into the channel on the other side of the dam, and this helps to reduce the resultant flow of channel X towards dam. Referring in particular to FIG. 1, fluid bearing the cells is supplied from vial C/AW into a microchannel 4. At the same time a buffer fluid serves as an attenuating fluid and is provided in the vial DA and flows in the same direction as the cell bearing fluid (ie upwardly in FIG. 1) and at the dam walls 1, 2 and 3 some of the attenuating fluid will flow over the dam walls to ensure that the cells dock gently against the dam walls forming three zones of cells that are gently docked and immobilised in a line along the dam walls. Of course the liquid pressure of the attenuating fluid must be less than that of the cell bearing fluid otherwise the cells will not dock at all, but is preferably sufficient to moderate the impact of the cells against the dam wall to improve their subsequent viability. Cells will be docked and aligned along the dam walls 1, 2 and 3 in the manner illustrated in FIGS. 2(a) and (b). FIG. 4, which will be referred to below in further detail, illustrates the docking of cells along the dam walls in the three zones.

Referring back to FIG. 1, it will be seen that the apparatus of this embodiment of the invention comprises two channels 10, 11 running from the top to the bottom (of course in this description terms such as "top", bottom", "upwardly", "downwardly", "left" and "right" and so forth refer only to the layout of features as shown in FIG. 1 and are used for convenience of illustration and should not be interpreted as limiting in any way) and connected to each other by the dam walls 1, 2 and 3. In the cell docking procedure, the left-hand (in FIG. 1) channel 10 can carry cell bearing fluid from vial C/AW to vial CW/A where cell waste is collected, while the right-hand (in FIG. 1) channel 11 can carry docking attenuator fluid from the vial DA to the vial CDW.

To generate a concentration gradient, two dilution intersections are created between dilution channels that extend horizontally across FIG. 1 and which connect to vials SDL and SDR. To one side of channels 10, 11 vial SDL connects to a channel 12 that bifurcates into two channels 13, 14 which connect to channels 10, 11 on either side of a central convoluted section of those channels. To the other side of channels 10, 11 vial SDR connects to channel 15 which bifurcates into two channels 16, 17 which again intersect with channels 10, 11 by means of dam walls at the same place as do channels 13, 14. Thus, a primary dilution intersection is formed at the junction of channels 10, 11, 13 and 16, while a secondary dilution intersection is formed at the junction of channels 10, 11, 14 and 17.

In this embodiment of the present invention, different concentration gradients may be obtained by simple or complex dilution the choice of which depends upon the chosen liquid levels in the vials as will be explained further hereafter. Regardless of the dilution mode employed, a concentration gradient is obtained by two consecutive dilutions, but as will be seen further below if the complex mode is used a greater concentration range is obtained. With either simple or complex dilution, however, an effective concentration gradient can be established and as will be seen below this concentration gradient is in the same direction of the line of cells docked on the dams walls following the docking operation.

Figure 3A:
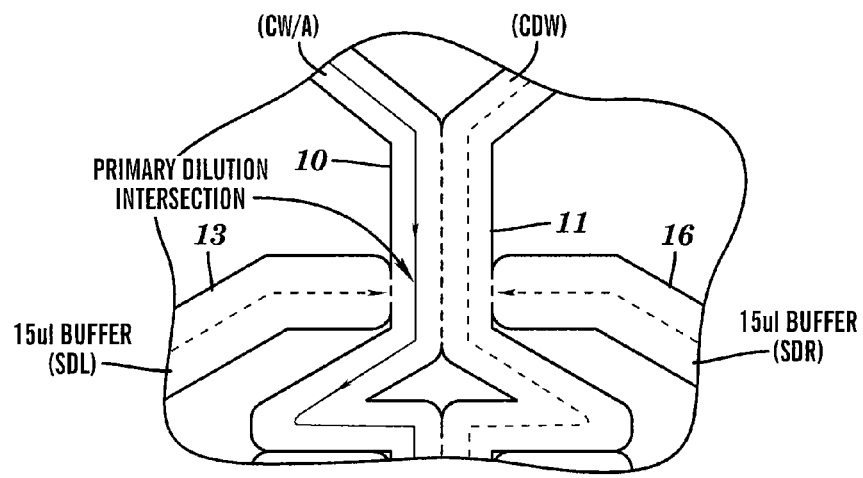
Figure 3B:
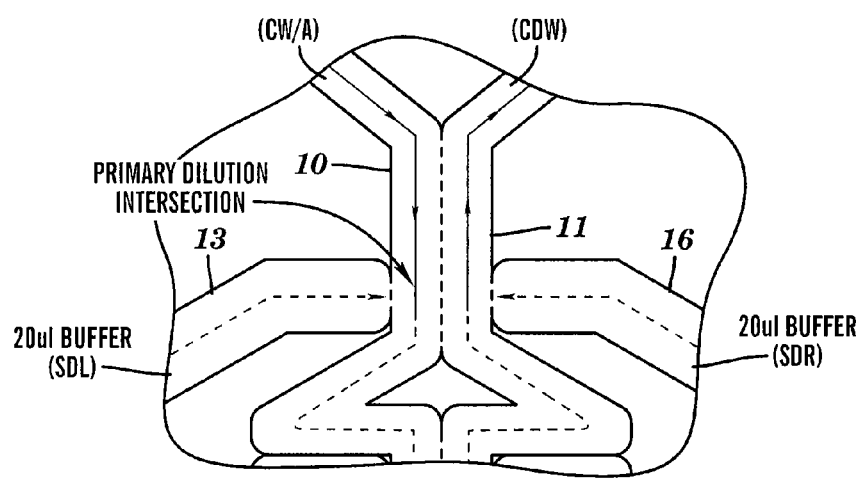

The generation of a concentration gradient will now be explained in more detail with reference to FIG. 3, and with reference to an example in which a fluorescent dye such as acridine orange (AO) is used to enable the concentration gradient to be seen visually. The only difference between the simple and the complex modes is the dilution mechanism at the primary dilution intersection. Simple mode dilution is shown in FIG. 3 and is similar to dilution at a conventional T-intersection. Analyte (AO) runs from CW/A vial in channel 10, while buffer streams come from vial SDL through channel 13, SDR through channel 16, and from vial CDW through channel 11. Analyte and buffer join at the primary dilution intersection and start to diffusively mix along channels 10, 11 downstream. As a result, a concentration gradient is established downstream from the intersection. FIG. 3(b) shows complex mode dilution. In this mode, analyte stream from CW/A is allowed to flow into the CDW vial (which is empty). Under this condition, together with a comparatively large liquid pressure coming from the SDL and SDR vials, only a minute amount (diffusion dependent) of analyte molecules can be carried by the buffer stream to flow downstream. A much greater dilution gradient is therefore expected in the complex mode as compared with the simple mode.

Although the difference between the two dilution modes is only in the manner of the dilution at the primary dilution intersection, the presence of the secondary dilution intersection is strongly preferable since the presence of the second dilution intersection results in a greater range of concentration over the three zones.

A practical embodiment of the present invention will now be described with reference to a typical experiment of the type for which the present invention is particularly suitable. In particular, in the following example an embodiment of the invention will be used to calculate the threshold ATP concentration that induces calcium uptake in HL60 mammalian cells.

In this example HL60 cells (leukemia, promyelocytic) were suspended in 0.5 ml fresh RPMI 1640 with Pluronic F-127 (1% w/v final) and Fluo3-AM (2 micro molar final). After 30 minutes of incubation at room temperature, cells were re-suspended in (Hank's balanced salt solution) HBSS before loading into the apparatus.

The example was carried out with an apparatus as shown in FIG. 1 and manufactured as described above. Before use, the etched quartz plate and a PDMS cover were touch-bonded and irradiated with UV light for 10 minutes in a bio-safety cabinet. After filling up micro-channels with buffer by capillary action, the apparatus was securely mounted on the stage of confocal microscope. Introduction of various fluids was implemented by using a 2-20 1 auto-pipette (HLT pipette-mate). An Axiovert 100M confocal microscope (Carl Zeiss) was used for data acquisition. Profiling data analysis mode was employed to present PMT response along a specific line in the apparatus. All fluorophores were excited by Argon (488 nm) laser. An emission filter 505-530 nm was used for Fluo-3 and AO while a 560 nm (long-pass) filter was used for ethidium bromide (EB) study. Scanning parameters were kept identical throughout all experiments for a particular fluorophore.

In this example, first of all a viability test was carried out to confirm that after docking a sufficient number of living cells were safely docked, and then a concentration gradient was made visible by a fluorophore. When the presence of a viable number of docked cells, and the creation of a concentration gradient were confirmed, the threshold concentration for calcium uptake was calculated using the apparatus of the invention, and then the results compared with an experiment using conventional serial dilution techniques.

Furthermore, in this experimental test of an embodiment of the apparatus, the following different liquid level programs (LLP) for the six vials were used and will be referred to in the following description:

TABLE 1

| | Liquid level programs (LLP) used | | | | | |
|---|---|---|---|---|---|---|
| LLP | Operations | SDL | CW/A | CDW | SDR | DA | C/AW |
| A | Cell docking | 20 | 0 | 0 | 0 | 4 | 5 (cells) |
| B | AO/EB staining | 10 | 10 (AO/EB) | 10 | 10 | 0 | 0 |
| C1 | Simple mode | 15 | 5 (AO) | 5 | 15 | 0 | 0 |
| C2 | Complex mode | 20 | 5 (AO) | 0 | 20 | 0 | 0 |
| D | ATP test | 20 | 5 (ATP) | 0 | 20 | 0 | 0 |

Unit of all values are in μL.

In the cell docking step, LLP A is used and cell bearing fluid is supplied from vial C/AW, while a docking attenuator fluid is supplied from vial DA. The liquid level in DA is slightly less than that in C/WA so that the liquid pressure on the DA side of the dams 1, 2 and 3 is slightly less such that gentle docking takes place of the cells along the dam 1, 2 and 3 in the three zones. In order to ensure that the mammalian cells were alive after docking prior to on-chip cell reaction, an AO/EB staining experiment was carried out 20 minutes after the docking procedure using LLP 2. As shown in FIG. 4, about 80 HL60 cells were aligned on a dam structure, 91% of the docked cells still viable as shown by the AO staining test. Living cells (AO stained) were in yellow while dead cells (both AO and EB stained) were in red.

Figure 5:
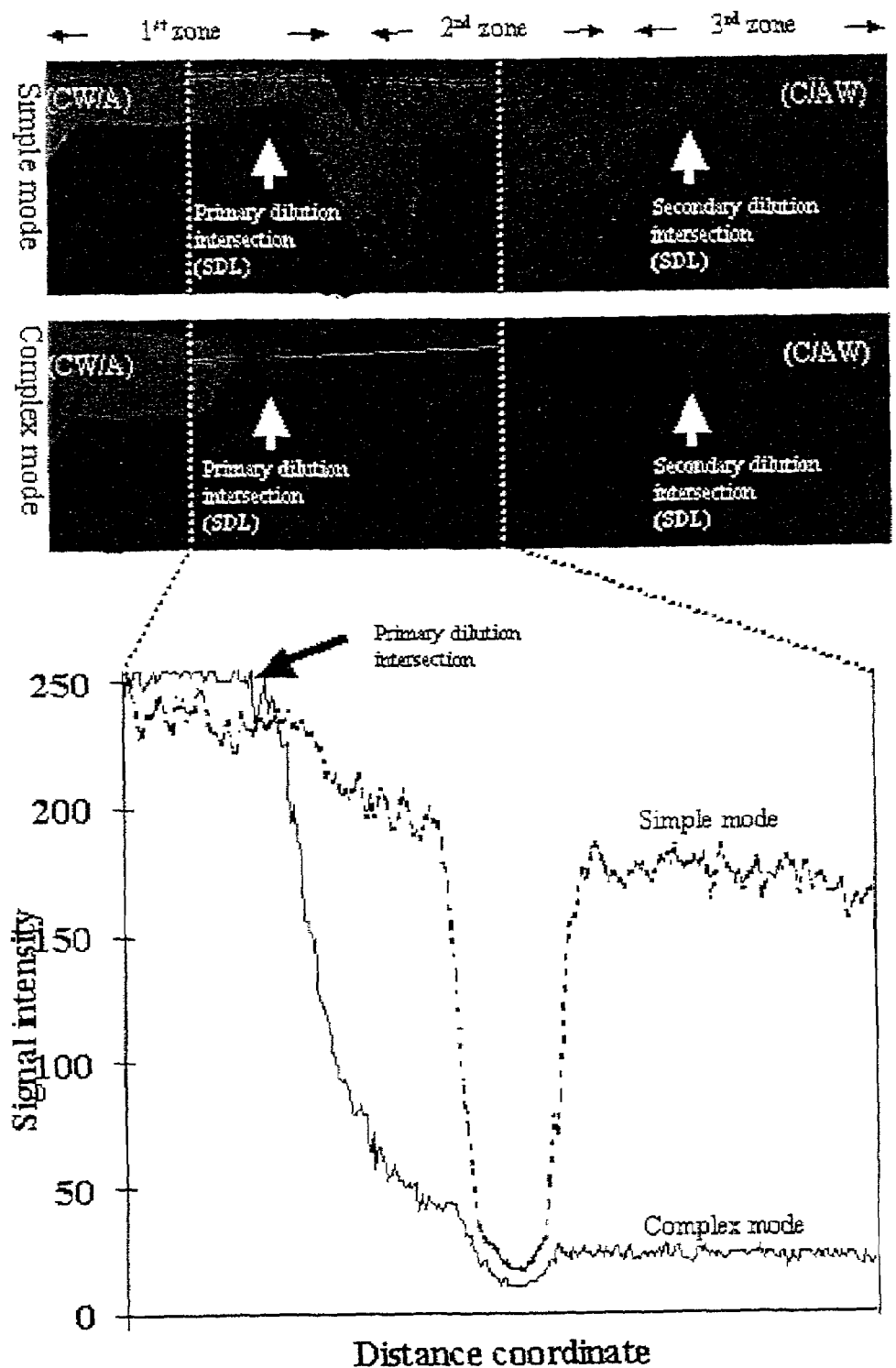

Similar to the cell docking process, analyte concentration could be manipulated by changing liquid levels in the vials to a different liquid level program program (LLP). FIG. 5 showed two concentration gradients (acridine orange, 33 μM) generated by LLP C1 (simple mode) and C2 (complex mode) as listed in Table 1 below. In the simple mode of dilution, analyte was diluted to 80% of its original concentration between $1^{st}$ and $2^{nd}$ zones. In contrast, a 15-fold dilution was observed in the complex dilution mode in the same zones. This dynamic change in dilution performance was produced at a single intersection by simply controlling the LLPs.

FIGS. 4 & 5 demonstrate that an apparatus according to the present invention is capable of manipulating mammalian cells and safely docking them into a desired position while retaining high viability, and at the same time enabling an analyte concentration gradient to be established. It should also be noted that the concentration gradient is in the same direction as the line of cells that are docked in the three zones. This is highly advantageous in that in a single experiment the effect on the cells of an analyte over a range of analyte concentrations can be seen directly in a single image.

Mammalian HL60 cells uptake extracellular calcium ions when the buffer ATP concentration is beyond a particular level. The minimum ATP concentration required to induce calcium uptake is referred as the threshold concentration. In this example of the use of an embodiment of the invention, cell docking and analyte concentration gradient were combined to determine the threshold concentration of ATP-dependent calcium uptake.

Figure 6:
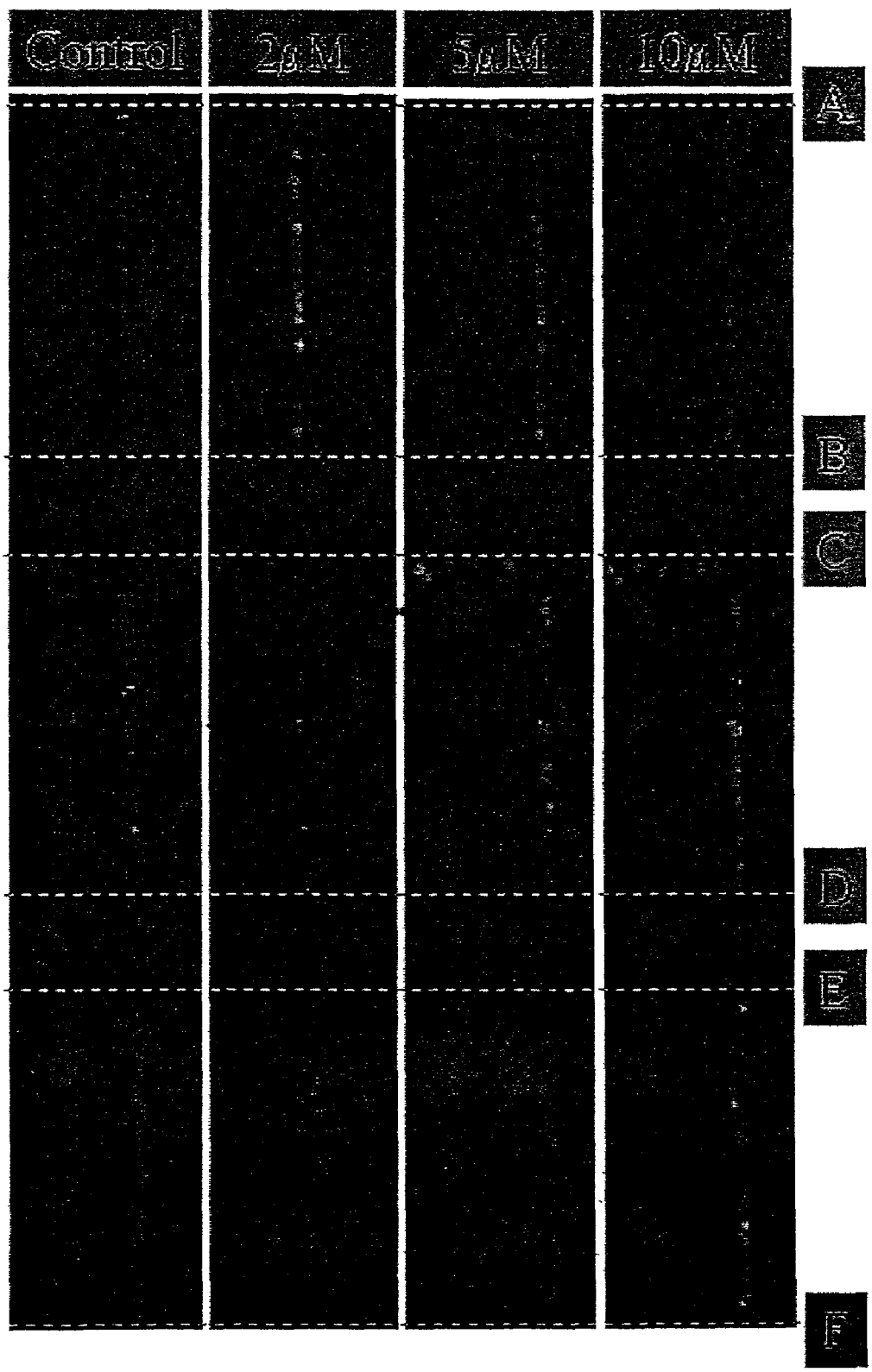
Figure 7:
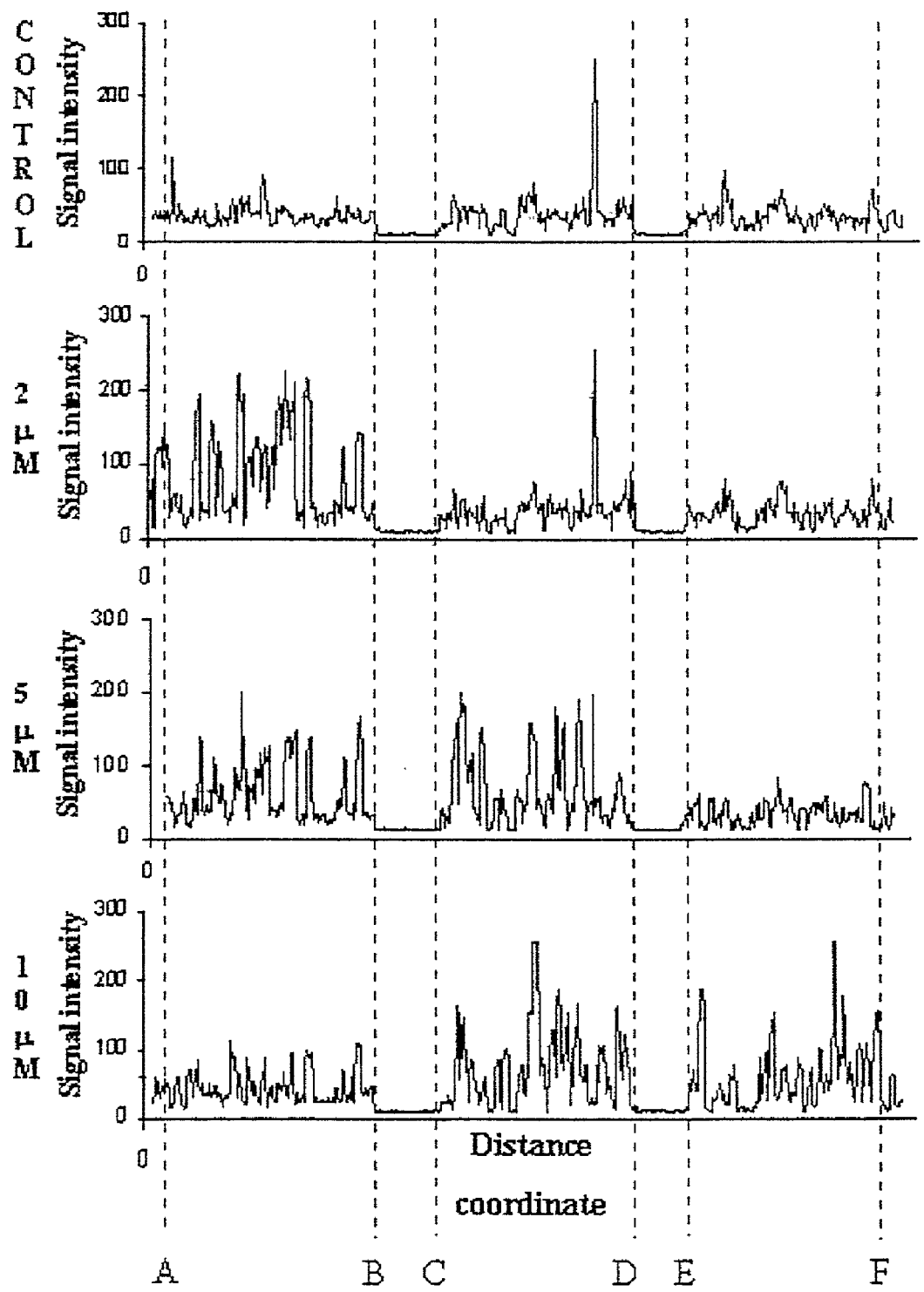

The fluorescence images of the microchip under different conditions are shown in FIG. 6, with about 80 docked cells along the dam. Corresponding fluorescence intensity along the line of the docked cells is shown in FIG. 7. In the "control" image and intensity measurement, the background cellular signal was due to the presence of intracellular calcium in HL60 cells.

Figure 2:
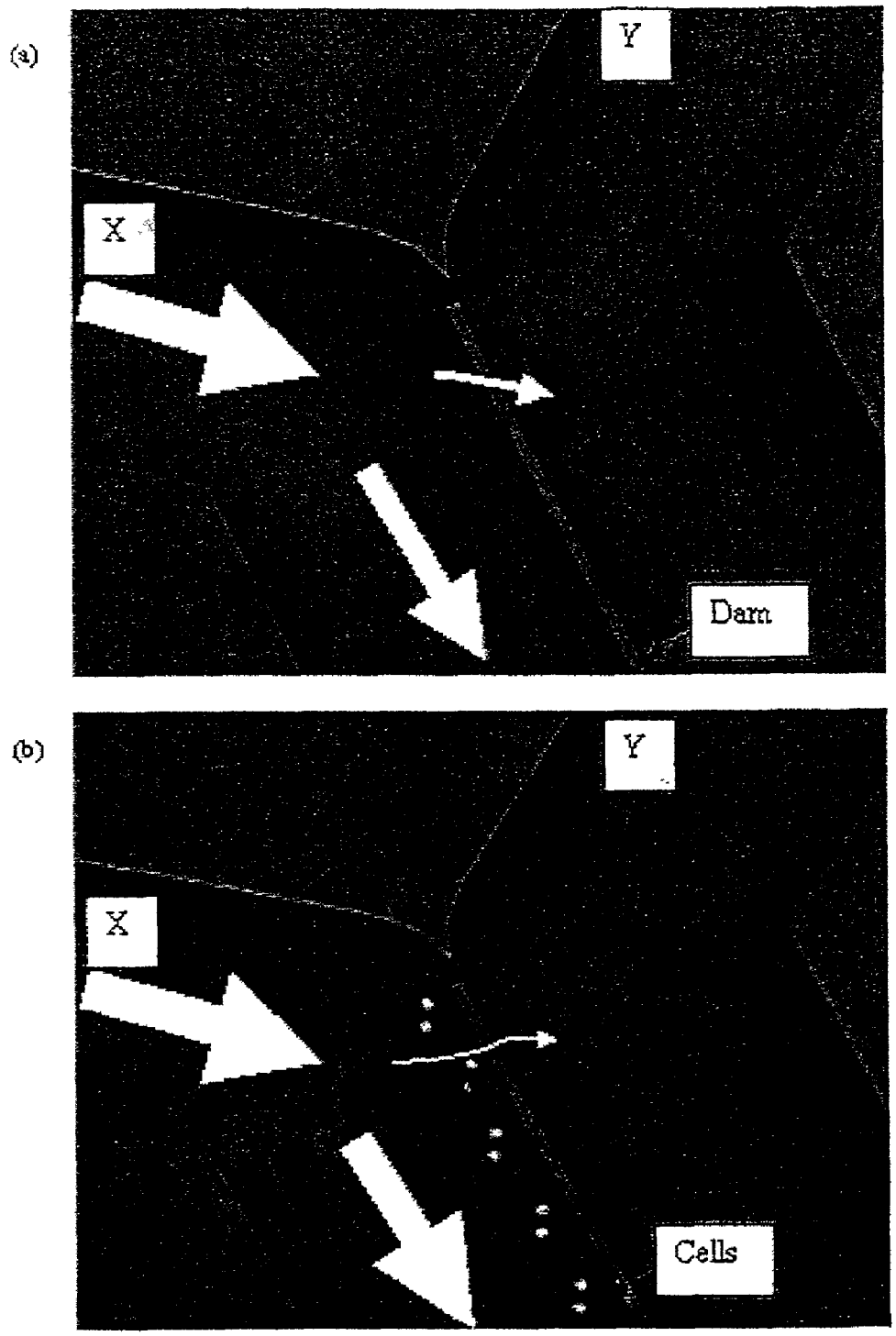
FIGS. 2(a) & (b) are schematic views showing the fluid flow during cell docking, FIGS. 3(a) & (b) are schematic views showing the fluid flow during dilution.

When an ATP solution (2 μM) was loaded into the CW/A vial, the cellular signal intensity was increased by 3-fold in the first zone (A to B) as compared to other zones (FIGS. 6 & 7, 2 μM images). The ATP threshold concentration can therefore be visualized as being between points B and C.

After washing with buffer, the same batch of docked HL60 cells were exposed to higher ATP concentrations. Using the same LLP, the threshold concentration range shifted downstream with increasing analyte concentrations. As shown in FIGS. 6 & 7, with 5 μM ATP loaded into the apparatus, the cellular fluorescence intensity-in the first (A to B) and second (C to D) zones were enhanced. The threshold concentration range was shifted to the zone between points D & E. Repeating this process with 10 μM ATP, the Ca-related fluorescence in all cells in all zones were excited, (the signal intensity at the first zone was relatively weak due to desensitization from multiple ATP stimulations.).

The experimental results obtained above indicated that the threshold ATP concentration was at a range below 2 μM. The ATP concentration gradient along the dam structure needs to be estimated in order to obtain the range of threshold concentration for this reaction.

Similar to many microfluidic systems with low Reynolds number, flow nature is laminar within the micro-channel network and the Bernoulli equation can be applied to an apparatus of the present invention:

$$H = hf = \lambda L v2/2dg \tag{1}$$

where H=liquid level, λ=resistance factor, L=length of channel, v=flow velocity, d=waterpower diameter of channel and g=gravity acceleration. Using this equation, a relationship between liquid levels H and flow quantity Q can be derived:

$$H = RQ + KQ2 \tag{2}$$

where parameters R and K depends on the geometrical profile of the channels. For the apparatus of this embodiment, the second term in Equation (2) is much less than the first one and can be neglected, so equation (2) can be simplified as:

$$H = RQ \tag{3}$$

Analyte diffusion should also be taken into amount for dilution in this embodiment of the invention. An analytical equation can be used to describe concentration distribution after lamina mixing:

$$C(t,x) = \frac{1}{2} C_0 \sum_{n=-\infty}^{\infty} \left\{ \mathrm{erf} \frac{h + 2nl - x}{2\sqrt{Dt}} + \mathrm{erf} \frac{h - 2nl + x}{2\sqrt{Dt}} \right\} \tag{4}$$

where C(t, x) is the concentration at time t and at point x, D=diffusion coefficient (D=3.68*10-6 cm2/s for ATP), t=time, 1=width of channel, h=width of the initial distribution, and $C_0$ is the concentration before intersection. A detailed description of the mechanical model of the apparatus of the present invention and one possible approach to calculate the concentration of an analyte within the channels will be described further below.

Figure 8:
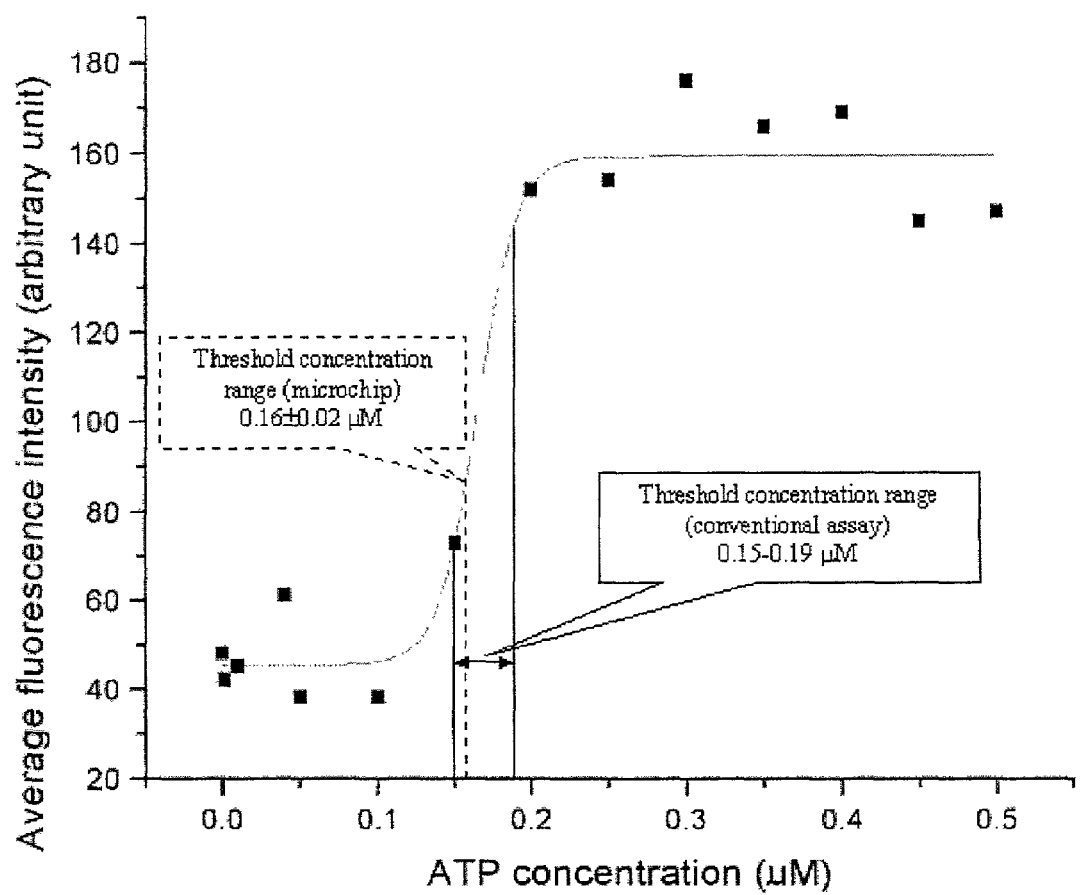
FIG. 8 is a plot of ATP threshold concentration obtained by conventional techniques for comparison purposes.

The ATP concentration gradient along the dam structure was estimated according to the above computational model. Combining the results obtained in 2 μM and 5 μM ATP stimulations, the threshold concentration was estimated within a range of 0.16±0.02 μM. The threshold concentration was also determined using conventional fluorescence measurements. FIG. 8 shows the results obtained from 13 individual serial dilution experiments. The threshold concentration range was determined to be 0.15-0.19 μM, which is in good agreement with the result obtained using the embodiment of the present invention.

Figure 9A:
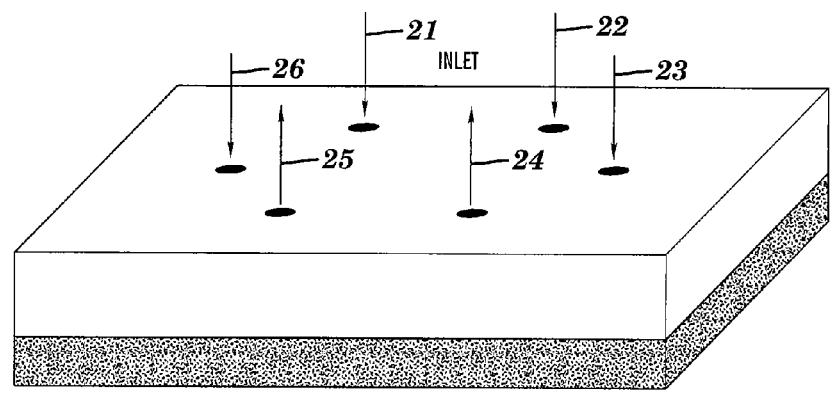
FIGS. 9(a)-(c) show an apparatus according to an embodiment of the invention used for modelling fluid flow and the generation of concentration gradients, FIGS. 10(a) and (b) show the fluid flow in the simple and complex modes.
Figure 9A:
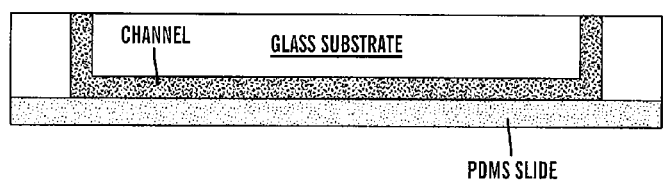

An example will now be given for a method of generating a known concentration gradient and for calculating the concentration gradient. FIG. 9(a) shows the microfluidic chip used in this example. The chip was made of glass substrate and PDMS cover using traditional photolithography and wet etching methods. Briefly, the glass wafer was deposited with a layer of photoresist, and a contact mask was used to expose the photoresist layer with UV light through the mask. Subsequent development in an organic solvent allowed the removal of exposed portions of the photoresist, leaving a polymerized resist pattern with high chemical resistance. Hydrofluoric acid (HF) wet etching was used to produce a channel structure and the remaining photoresist was stripped off. Access holes (3 mm diameter) were drilled at the inlets and outlets using a diamond coated drill bit. A PDMS (Sylgard 184, Dow Corning, Midland, Mich.) elastomer membrane (2 mm thickness) was prepared and was used to seal the microchannels to form a closed sandwich structure. Before each experiment, the glass substrate was washed with detergent several times. After drying, the microfluidic network was sealed by the PDMS cover with pressure.

0.01% Acridine Orange (GIBCOBRL) (AO) was dissolved in 20 mM TE buffer. 0.4% Trypan Blue (TB) Stain (GIBCO-BRL) was prepared according to given instructions. All solutions were made from reagent grade chemicals and filtered by disposable syringe filter unit (MFS 25, ADVANTEC MFS, Inc.) with pore size of 0.25 m before use. A laser confocal microscope (Axiovert 100M, Carl Zeiss) was used to acquire fluorescence images. Profiling data analysis mode was employed to present PMT response along a detection line. For Acridine Orange (AO) related experiments, Argon (488 nm) laser and emission filter (505-530 nm) were used. The same laser and long pass emission filter (585 nm) were used for Trypan Blue (TB) analysis. All scanning parameters were kept identical for a particular fluorophore throughout all experiments.

Figure 9B:
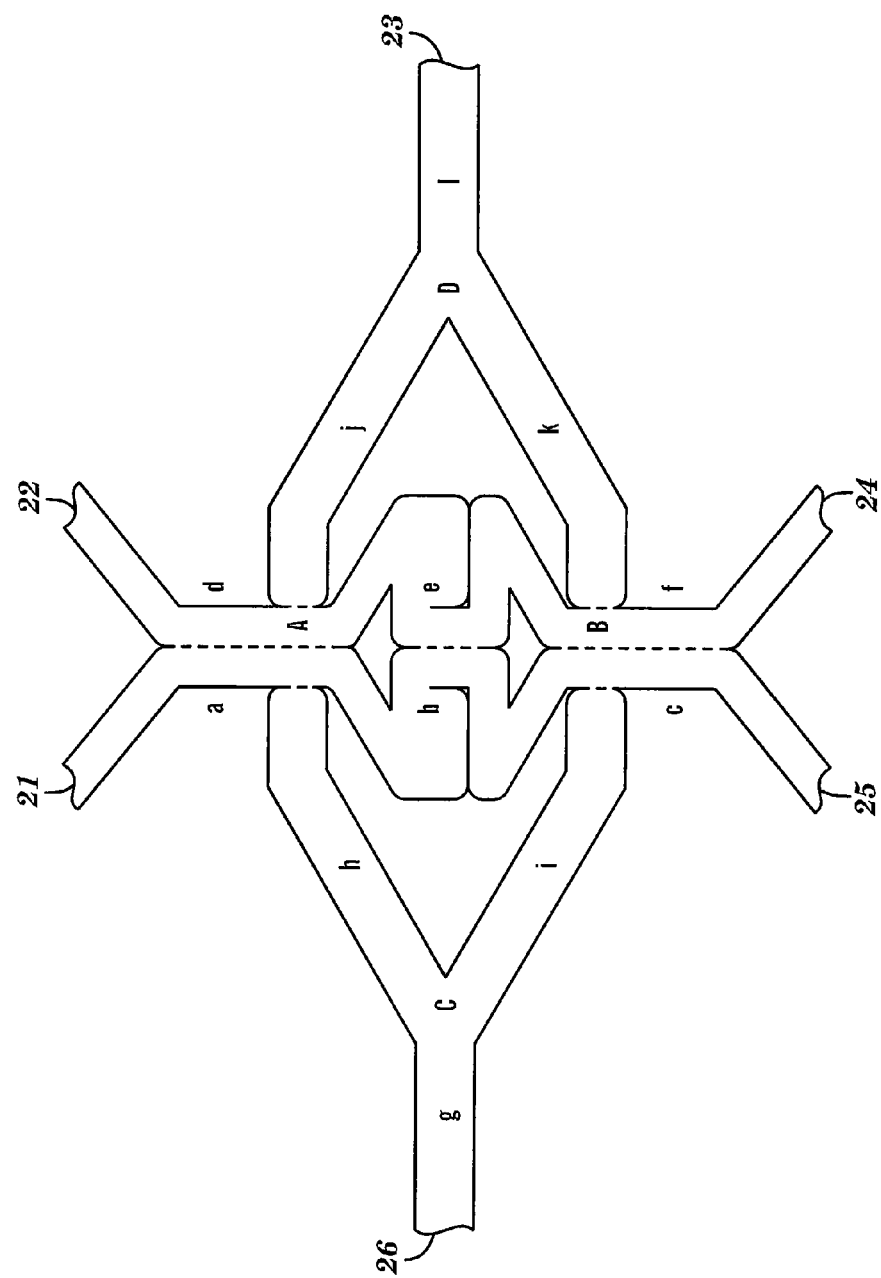

As shown in FIG. 9(b), the fluorescent dye solution (AO or TB) was introduced via inlet 21 and the fresh buffer solution was introduced through inlets 22, 23 and 26 and traveled down to outlets 24 and 25 (simple control mode, and in complex control mode, no fluid was loaded into inlets 22). The entire image of the microfluidic chip was captured by the laser scanning confocal microscope, and the concentration gradient established in serial microchannels 21, 22 and 23 were evaluated by profiling analysis mode.

Figure 9C:
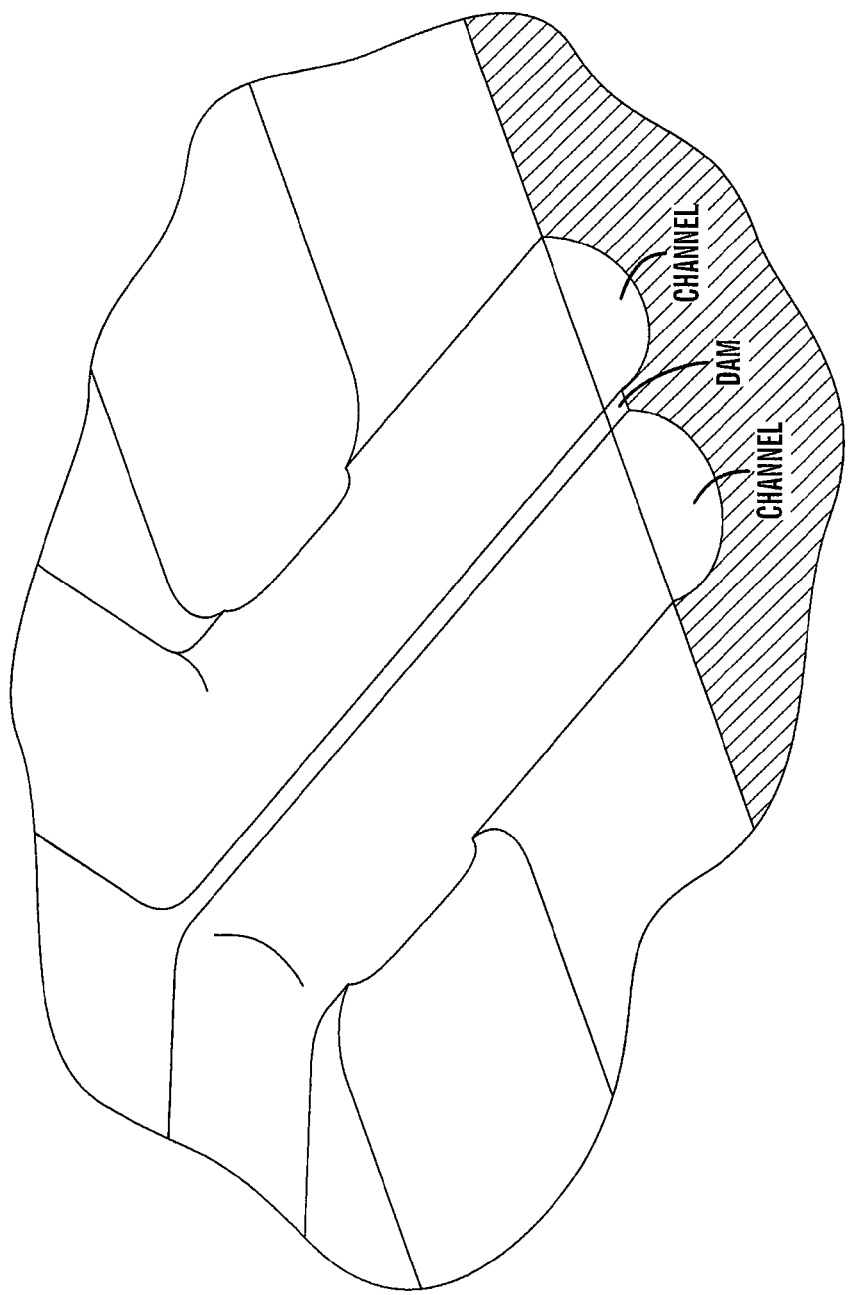
Figure 10A:
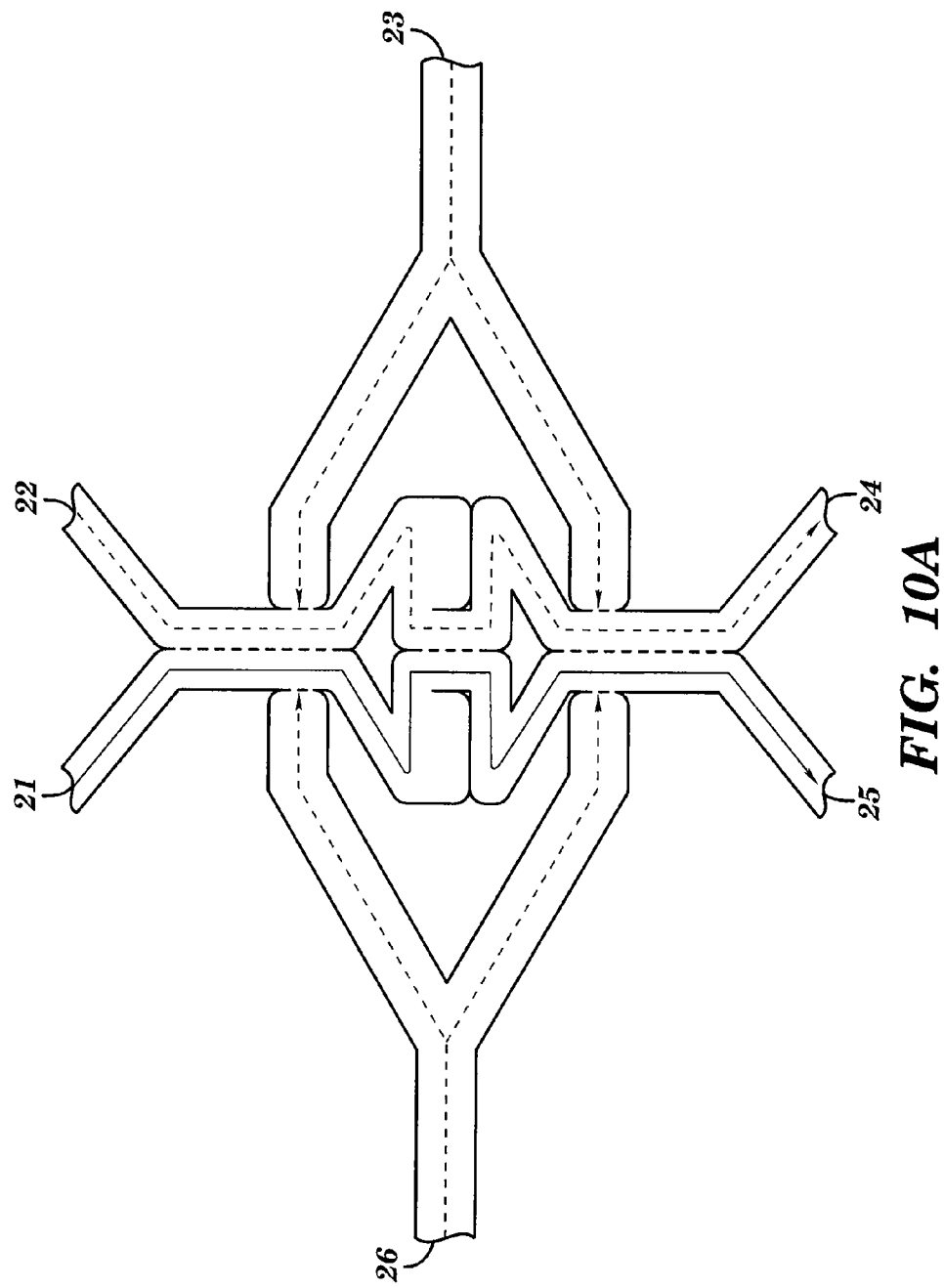

Referring again to FIG. 9(a), the apparatus used in this example comprised four inlets (21, 22, 23 and 26) and two outlets (24 and 25). The microchannel network is composed of two symmetric sections, divided by three dams in the middle (dams being denoted by dotted lines in FIG. 9(b) and the sketch in FIG. 9(c). Different dye solutions were introduced via inlet 21, and fresh buffer was introduced via inlets 22, 23, and 26. All solutions were loaded almost simultaneously into this microfluidic chip and flowed from inlets to outlets. Two control modes, termed simple and complex as described previously, were used to manipulate liquid pressures. In the simple control mode (FIG. 10(a), solid line is the dye solution fluid, and dashed line is the fresh buffer fluid.), liquid pressure in inlet 21 was always the same as that in inlet 22, while liquid pressure in inlet 23 was equal to inlet 26. As a result, no net fluidic force could push the dye solution across to the symmetric counterpart, and leakage at each intersection was negligible. Diffusion through each dam should be the only mixing mechanism between the two symmetric counterparts. However, the dam structure reduces the depth of the channel to ~5 μm and leads to the small interface area between adjacent fluids, which hinders dye diffusion across to the symmetric counterpart. In addition, the duration of solution flowing near the dams is very short, which further decreases the diffusion. As a result, the diffusion of dye across to the symmetric counterpart was minimal in the simple control mode.

Under the simple control mode, the dye solution from inlet 21 and the fresh buffer from inlet 26 mix at intersections A and B (FIG. 14(a)). Due to low fluidic flow rate (less than 100 μm/s, according to the computation described below), fluid behaves as laminar in this microfluidic network with low Reynolds numbers. (The Reynolds number $R_e$ is a non-dimensional parameter relating the ratio of inertial to viscous forces in a specific fluid flow configuration, and laminar flow occurs in fluidic systems with $R_e$<2000. In the current microfluidic network, $R_e$ is often less than 10). After mixing at these intersections, the dye solution and the fresh buffer flow into downstream microchannels 22 and 23 side by side and diffusion is the main factor for mixing during this period. The dye solution is consecutively diluted in the two intersections A and B by the fresh buffer, such that the concentrations in channel a, b, and c are different, and a discontinuous concentration gradient is generated in these serial microchannels.

Figure 10B:
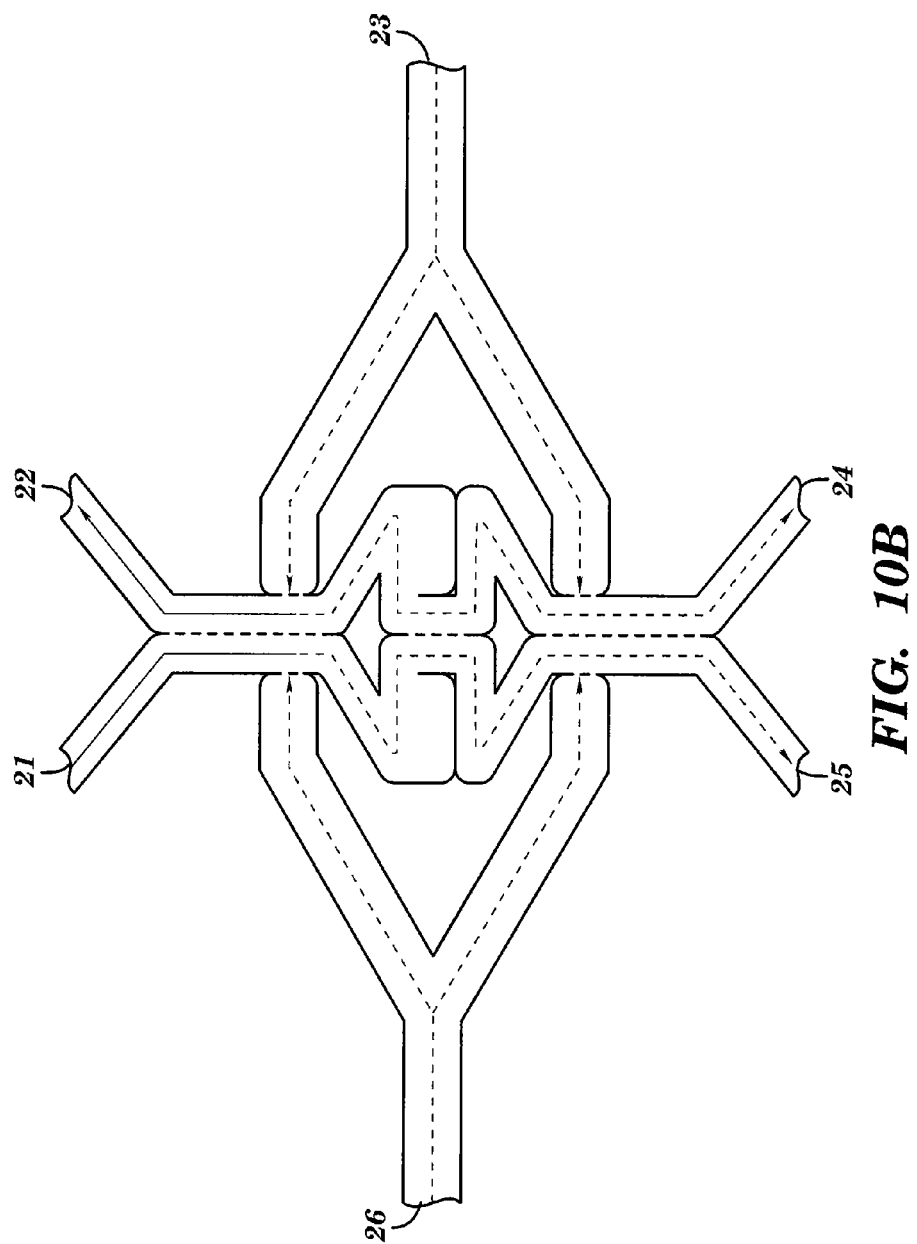

In the complex control mode (FIG. 10(b)), the dye solution was introduced from inlet 21 and fresh buffer was introduced from inlets 23 and 26. Unsymmetrical liquid pressures are generated between the symmetrical inlets. Because there is a higher liquid pressure in inlet 26, which is different from the simple mode, the dye solution can not flow into channel b, but flows to channel d instead. Fresh buffer from inlet 26 is divided into two parts at intersection A, with only a part that can flow into channel 22. Some dye molecules can diffuse from intersection A to channel 22. As a result, the quantity of dye in channel 22 is much lower than that generated from the directional mixing between the dye solution and the fresh buffer in the simple mode.

A theoretical model with a numerical solution for the concentration gradient generated in this microfluidic chip will now be described.

Bernoulli equation describing laminar flow in circular pipe is given as:

$$\Delta H = hf = \lambda L v^2 / 2dg \quad (5)$$

where H is the liquid level (Δ is a variety), λ the friction factor, L the equivalent length, v the flow velocity, d the diameter of pipe, and g is gravity acceleration (9.8 m/s²), respectively. L can be calculated by channel length l and another parameter $l_e$, $$L = l + l_e = l + \Sigma \xi_i d / \lambda \quad (6)$$

where $l_e$ is a length converted from the resistance impact of pipefittings in a channel. Here Σ is a sum symbol and $\xi_i$ is the loss coefficient that describes the impact of each pipefitting such as connection, flow divider, bend and elbow, reducer, and valve. Friction factor λ can be replaced by Reynolds number $R_e$:

$$\lambda = 64/R_e = 64 \gamma / vd \quad (7)$$

where γ is the kinematic viscosity. Velocity v can be calculated by flow quantity Q and sectional acreage A:

$$v = Q/A \quad (8)$$

While the above equations are derived for the computation of flow in a circular pipe network, they can also be used to compute the flow in a noncircular pipe where the diameter of circular pipe in these equations must be replaced with the hydraulic diameter of noncircular pipe. A hydraulic diameter is described as $$d = \sqrt{4A/\pi} \quad (9)$$

According equations (5)-(9), the relationship between the difference of liquid levels, ΔH and the flow quantity Q can be derived as:

$$\Delta H = RQ + KQ^2, \; R = 128 \gamma l / g \pi d^4; \; K = 8 \Sigma \xi / g \pi^2 d^4 \quad (10)$$

where R and K are parameters that can be calculated by geometrical profile of the channels (the results are shown in Table 2 below).

TABLE 2

| | Fluidic parameters | | | |
|---|---|---|---|---|
| Channels | Hydraulic diameter d (μm) | L (μm) | Σξ | R (10⁹s/m²) | K (s²/m⁵) |
| 1, 3, 4, 6 | 35.44 | 2880 | 0.3515 | 6.8979 | 18429.5 |
| 2, 5 | 35.44 | 275 | 8.02 | 0.72476 | 420498 |
| 8, 9, 10, 11 | 37.62 | 695 | 2.2955 | 1.44259 | 71130.6 |
| 7, 12 | 37.62 | 9280 | 0.0955 | 19.2623 | 2959.25 |

From Table 2, it is very clear that in this microfluidic channel network, the absolute value of parameter K is much less than that of parameter R. Meanwhile, in practice, ΔH is so low that the absolute value of Q is a decimal fraction in equation (10). The term KQ² is much less than RQ and can be neglected, and equation (10) is simplified as:

$$\Delta H = RQ \quad (11)$$

Figure 11:
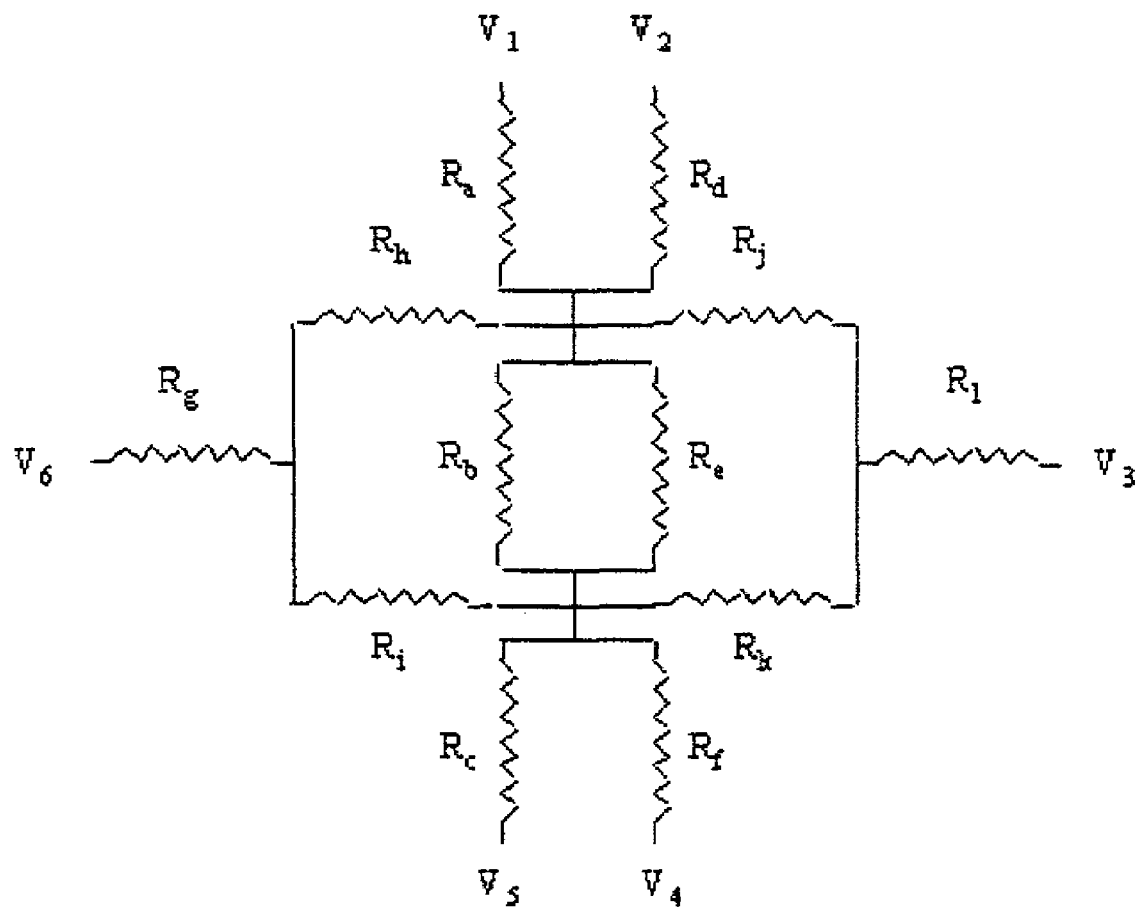
FIG. 11 shows an equivalent electrical circuit model, FIGS. 12(a) & (b) show mixing and diffusion in the simple mode.

This equation is very similar to the Ohm's law in electrics, where ΔH corresponds to voltage drop ΔV, R to electric resistance R, and Q to electric current I. Therefore, an electrical circuit model can be used to simulate this channel network (FIG. 11). Numerical methods for analysing electrocircuit networks could be used to compute flow quantity in every channel and to determine the mixing parameters at every intersection. In the simple control mode, equation (11) is applied to the six channels in the left side of this microchannels network ($\Delta H_i = R_i Q_i$, i=a to c, g to i). At the same time, flow quantity balance comes into existence at intersections A, B and C. All nine equations could make up a matrix. In the complex mode, equation (11) is applied to all twelve channels in this chip, and flow quantity balance exists at four intersections (A-D). A matrix including sixteen equations could be derived here. Solving these two matrices would determine the flow quantity of each channel in different control modes. The quantity distribution factor $r_i$ (i=a, b) between the fresh buffer and the dye solution at intersections A and B could also be obtained.

Figure 12:
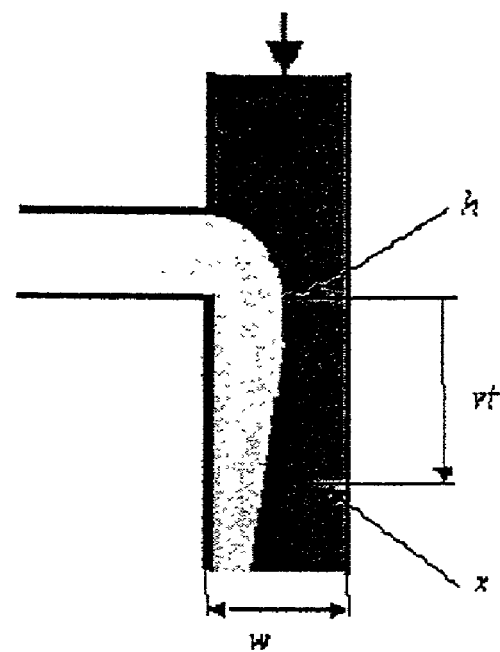
Figure 12:
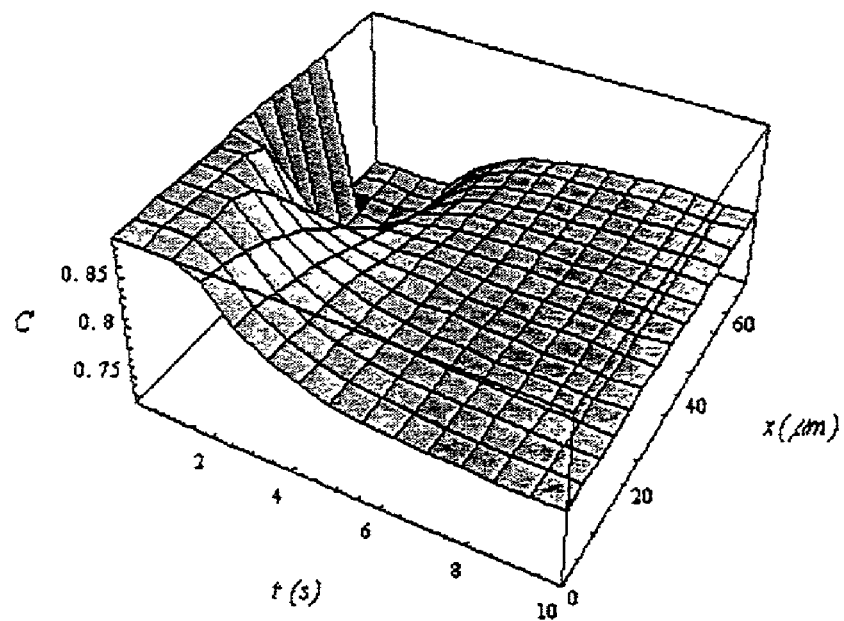

In the case of a laminar flow, after the fresh buffer and dye solution are combined into one channel, diffusion becomes the main mixing mechanism. An analytical equation could be used to determine the distribution of concentration in this microchannel after the diffusion:

$$C(t,x) = \frac{1}{2} C_0 \sum_{n=-\infty}^{\infty} \left\{ \text{erf} \frac{h + 2nw - x}{2\sqrt{Dt}} + \text{erf} \frac{h - 2nw + x}{2\sqrt{Dt}} \right\} \quad (12)$$

where C (t, x) is the concentration at time t and at point x, w the width of channel, and $C_0$ is the concentration before intersection, h is the width of the initial distribution and can be given by the quantity distribution factor $r_i$, h=$r_i$w (FIG. 12(a)). The final concentration gradient profile in this microfluidic network is simulated (FIG. 12(b) shows the distribution of concentration in channel 3, the concentration C was normalized with initial concentration $C_0$).

Figure 13:
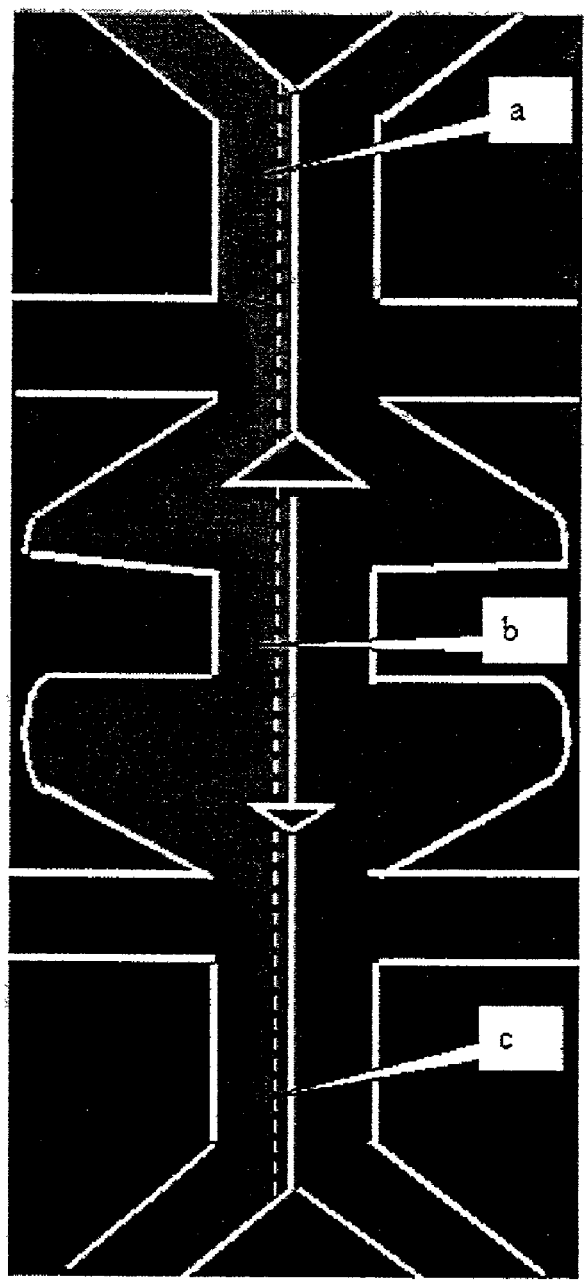
FIG. 13 is a fluorescence micrograph of concentration gradient of a dye in an embodiment of the invention.

FIG. 13 shows the concentration gradient of AO in the microfluidic network. The white lines identify the boundaries of the microfluidic channels not visible in this fluorescence micrograph. The images were taken when steady flows were formed in the microchannels about two minutes after the dye was introduced. Along the three channels a-c, the concentration gradient is visible due to the mixing of dye with fresh buffer at intersections A and B.

Figure 14:
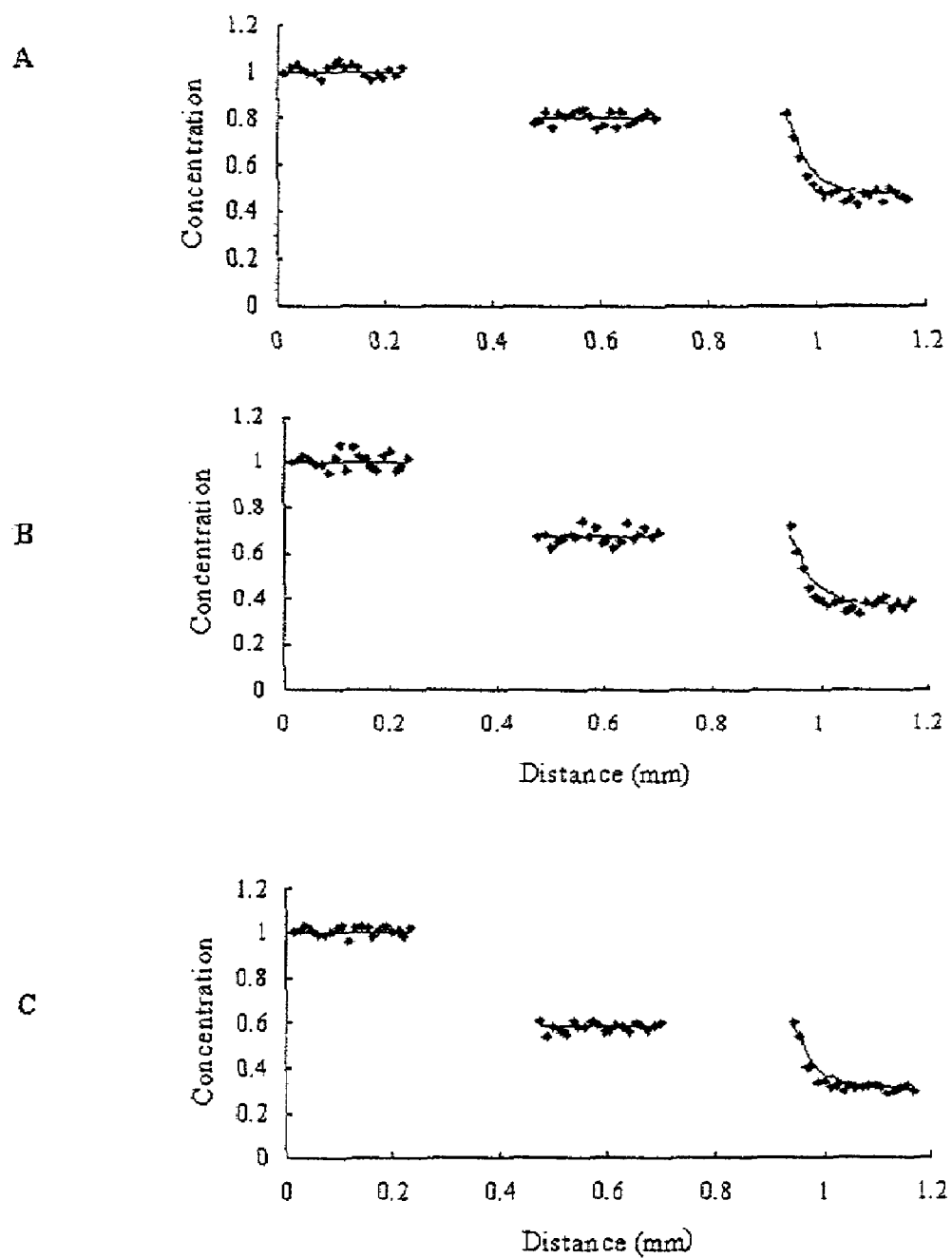
FIGS. 14(a)-(c) illustrate the effect on the concentration gradient of varying liquid pressure at one inlet.

FIG. 14 shows the fluorescence intensity profile along the detection line (the white dashed line in FIG. 13), which was ten micrometers away from the middle dam. The solid line is the computation data, and the dotted line is the experimental data. The highest concentration of dye is found in the channel a, and the concentrations in channel b and c gradually decline to form a discontinuous gradient. Within channel c, there is continuous concentration gradient. It can be postulated that flow behaves similarly to that in channel c where diffusion equilibrates exactly before subsequent mixing. Therefore, a long concentration gradient can be form in a series microchannels. The measured concentration profiles agree well with the numerical simulation, indicating that diffusion is the main mixing factor in these channels. If the liquid pressure distribution between inlet 21 and 26 are changed, the concentration gradient would change accordingly. In these three conditions in FIG. 14, the liquid pressure in inlet 21 is fixed at 18 Pa. When the liquid pressure in inlet 26 changes from 30 Pa (FIG. 14(a)) to 36 Pa (FIG. 14(b)) and 40 Pa (FIG. 14(c)), the concentration in channel b and c decreases in turn, so the discontinuous concentration gradient is broadened accordingly.

In a numerical simulation of the simple control mode, flow quantities in channels a, b and c could be described as:

$Q_a = 0.080234 h_1 - 0.021338 h_6$ $Q_h = -0.024635 h_1 + 0.021338 h_6$ where Q was the flow quantity in each channel (when Q>0, solution flow from inlet to outlet, Q=0, no flow, and Q<0, solution flow back to inlet) and h was the liquid level in each inlet. In example, MATHEMATICA software was used to carry out all numerical computation. From these equations, it is clear that flow quantities are directionally related to concentration gradient and controlled by the ratio of liquid pressure in reservoir 26 to that in reservoir 21 (Table 3).

TABLE 3

Dynamic regulation of gradient

| | $Q_a$ | $Q_h$ | Concentration ratio |
|---|---|---|---|
| $h_6/h_1 > 3.76$ | <0 | >0 | Nil |
| $3.76 > h_6/h_1 > 1.15$ | >0 | >0 | $1:Q_a/Q_b:Q_a/Q_c$ |
| $h_6/h_1 < 1.15$ | >0 | <0 | Nil |

When liquid pressure ratio $h_6/h_1$ was more than 3.76, $Q_a$ was less than zero, and liquid flows back to reservoir 21 and there is no concentration gradient. When $h_6 h_1$ was less than 1.15, $Q_a$ was larger than zero, and $Q_h$ was less than zero, some of the dye solution flowed into channel h, and there was no dilution at intersection A and no concentration difference between channel a and b. When $h_6/h_1$ is more than 1.15 and less than 3.76, both $Q_a$ and $Q_h$ are larger than zero, and a concentration gradient forms along microchannels a, b and c. In this case, the ratio of concentration of channel a to b and c is $1:Q_a/Q_b:Q_a/Q_c$.

Using this method, through changing the liquid pressure in inlet 26, the concentration gradient in this microfluidic network can be modulated. The inlet 26 can be used as a tuner knob in this concentration gradient generator. If the liquid pressure in inlet 26 is increased, the concentration in channel b and c would gradually decrease, and after a critical level, the dye solution from inlet 21 could no longer flow into other microchannels and the concentration changes to zero. This could be used to wash the microchannels with fresh buffer.

Figure 15:
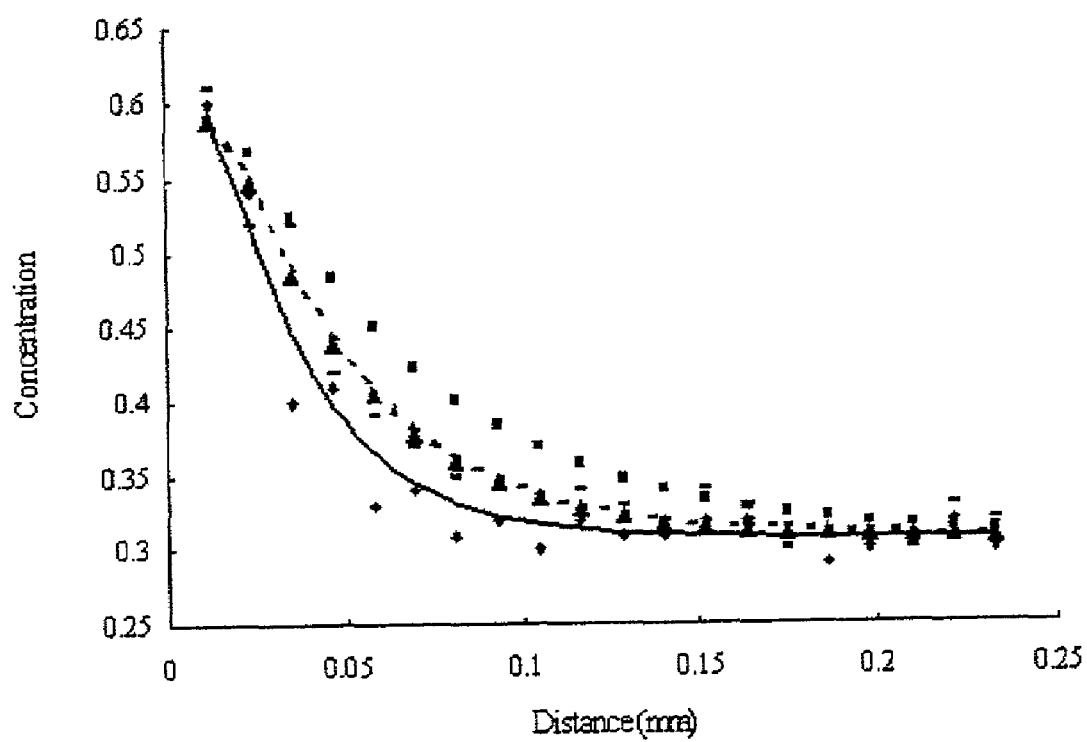
FIG. 15 illustrates the effect of diffusion coefficient on the concentration gradient.

Because diffusion is used as a main method to mix the laminar flows in these channels, the diffusion coefficient affects the continuous concentration gradient within microchannel c. Two dyes, AO and TB, with different diffusion coefficient (The diffusion coefficients D of AO and TB in water at room temperature are given $4.4 \times 10^{-6}$ cm$^2$/s and $3.0 \times 10^{-6}$ cm$^2$/s, respectively) may be used to confirm this. By applying the same liquid pressure among all vials, the concentration gradient is found to be different between the two dyes as shown in FIG. 15. The computed gradient of AO declines more quickly than that of TB ("♦" dots are AO, "-" TB) because the greater diffusion coefficient of AO results in faster diffusion. In order to achieve the same concentration gradient profile between two dyes, the liquid pressure applied for TB dye can be adjusted to a lower flow rate for TB.

In these results, the measured values ("♦" dots are AO, "-" TB) of concentration gradient in channel 23 declined more quickly than the computation value. This is probably because the mixing of two fluidic streams is not completely parallel and a small vertical mixing component contributes to the enhanced diffusion. A correction factor σ may be introduced here, $D_r = \sigma D$. If σ=1.4, and the corrected computational curve shows improved fitting to experimental results (solid line was the corrected result of AO and dashed line was the corrected result of TB).

Figure 16:
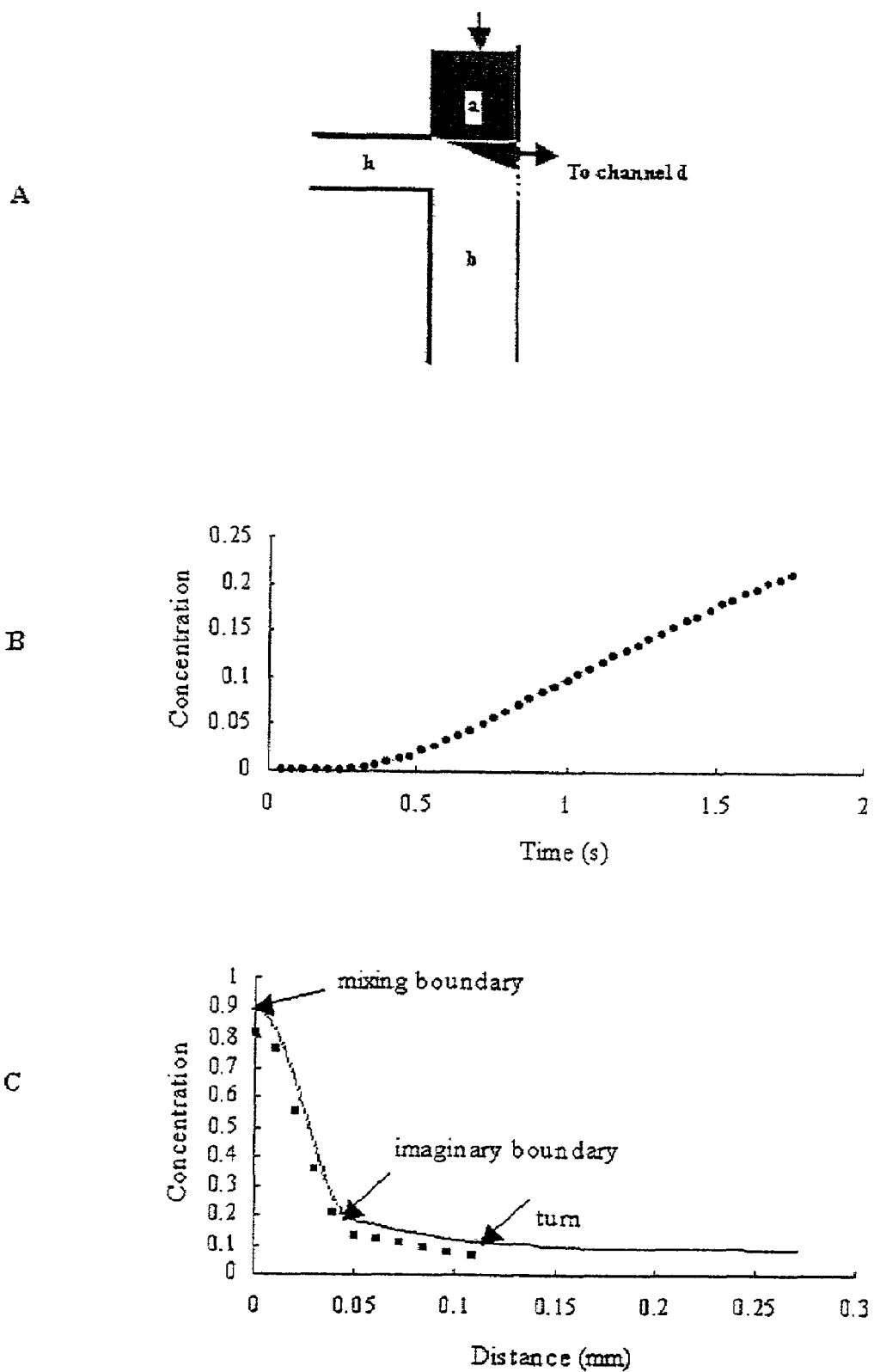
FIGS. 16(a)-(c) illustrate the concentration gradient in the complex mode.

To generate a great gradient in the simple control mode, only a little dye solution is allowed to flow from channel a to b, i.e. $Q_a$ must much less than $Q_b$. In this case, small fluctuation of flow leads to large change of concentration gradient with significant error in the experiments. Sometimes the dye solution may not flow into the microfluidic channel. Therefore to generate large gradient it is preferable to use the complex control mode in which unsymmetrical liquid pressure is generated in symmetrical inlets. Due to the large liquid pressure in reservoir 26 and the small pressure in reservoir 22, dye solution can not flow from reservoir 21 into channel b, but can flow to channel d. A part of the fresh buffer from inlet 26 flows into channel b, and the rest of the buffer flows into channel d with the dye solution. The dye solution and the fresh buffer are mixed and diffused at intersection A, and some dye molecules diffuse into the fresh buffer flowing into channel b. As a result, the concentration of dye in channel b is much lower than that in the simple control mode, and a large gradient is generated between channels a and b. In the numerical simulation, there is an imaginary boundary between fresh buffer flowing to different channels (the white line in FIG. 16(a), and the broken line is the dam). Suppose that there are two diffusion processes. At first, dye molecules diffuse into the fresh buffer that flows to channel d and some dye molecules diffuse to the fresh buffer that flows to channel b. The two parts of fresh buffer have the same concentration at the imaginary boundary, and Equation (12) could be used to compute the concentration of dye in the first part. Integrating the quantity of concentration at boundary, the concentration of dye in the fluid to channel b can be calculated. The mixing and diffusion model at intersection A is given in FIG. 16(a), the concentration at imaginary boundary given in FIG. 16(b), and concentration gradient is given in FIG. 16(c) (along the white broken line in FIG. 13). In FIG. 16(c), experimental results (dots) were less than the simulation results (solid line) because dye molecules continuously leak from fresh buffer to channel d to fresh buffer to channel b, and the factual concentration at boundary is less than the computation (in simulation, these two process were thought independent).

It will thus be seen that the present invention, at least in its preferred embodiments, provides an apparatus in which cell docking and the creation of a concentration gradient are integrated, and furthermore in that the cells are docked along a line that corresponds to the direction of the concentration gradient whereby the effect of an analyte on a cell at a range of concentrations can be seen directly in a single viewing the cells.

The cell docking mechanism in this invention allows high efficiency cell transportation and gentle immobilization of fragile mammalian cells. These characteristics are indeed conflicts to traditional dams constructed perpendicular to the main flow route. Rapid particle transportation can be implemented by increasing liquid pressure (hydrodynamic pressure, air pressure, electrokinetic force, etc) in micro-systems, however, with conventional designs severe damage to fragile mammalian cells would occur when cells crash onto traditional dam structures under high pressure. On the other hand, if liquid pressure is reduced for cell blocking at traditional dams, cell transportation becomes unreasonably slow in traveling from vial to dam. Moreover, low liquid pressure is also attributed to causing serious cell adhesion on micro-channels. Because of the difficulties in creating efficient cell transportation with gentle cell immobilization, successful handling of mammalian cells with traditional dam structures is very difficult to achieve.

However, in the present invention the dam structure is constructed along the main flow route parallel to the principal flow direction and contributes minimal fluidic resistance against cell transportation. At the same time, fluidic pressure across the dam can be attenuated, an advantage for immobilizing fragile materials. In other words, cell flow velocity was considerably faster in main flow route than that of the flow running towards the dam structure. Consequently, both high efficiency cell transportation and gentle cell immobilization—which in the prior art are contradictory objectives—are achieved in preferred embodiments of the present invention.

Once a cell is docked on a particular location of the dam, fluidic flow at that location experiences more resistance than at other unoccupied locations. Cells driven by fluidic flow tend to dock on other regions until the dam is fully occupied. This dynamically changing liquid pressure initiated by cell docking leads to the formation of a single line of self-aligned HL60 cells as shown in FIG. 4. The automatic alignment of single cells is another unique feature of the present invention, which provides a more stable and reproducible environment for conducting biological experiments comparing than the traditional dam structures.

Firstly, as excess cells are driven away, the total number of cells docked by self-alignment can be reproducibly controlled by the length of the dam. This is in great contrast to traditional perpendicular dams where cells accumulate on the dams, forming multiple levels of cells with unpredictable quantity. Secondly, due to the consistency in generating a single line of cells, fluidic resistance along the main flow route is more or less constant throughout the experiment. In the traditional perpendicular dams, however, the fluidic flow varies with the amount of cells immobilized and the resistance changes drastically after the dam is completely blocked. Stable fluidic resistance along the main flow route enables flow quantity to be correctly estimated, which is crucial for integrating in-situ concentration gradient in the microchannels.

A further advantage of the present invention is the ability to generate easily a large dynamic range of dilution capability which is highly convenient for serial dilution experiments. It allows minimal human intervention in sample pre-dilution before microfluidic analysis. Compared with prior art single intersection dilution practices, the dynamic range of dilution is usually predetermined by the micro-scale architecture. Altering liquid pressure by liquid level or voltage usually results in insignificant change of dynamic range because of the fixed channel length ratio. Therefore, in the prior art a single intersection with large dynamic dilution range is difficult to achieve.

The invention claimed is:

1. An apparatus for on-chip monitoring of cellular reactions comprising:
    a surface formed with a plurality of channels for fluid flow and a first inlet for supplying a cell bearing fluid to a first of said channels, wherein a second of said channels extends parallel and adjacent to said first channel for at least a part of their length defining a plurality of separate spaced-apart zones and wherein said first channel and said second channel are separated over said at least one part of their length by a wall defining a plurality of separate spaced-apart dams, said wall comprising a first height and said plurality of separate spaced-apart dams comprising a second height and wherein said second height is lower than said first height, a respective one of said plurality of separate spaced-apart dams being disposed in a respective one of said plurality of separate spaced-apart zones, over which said plurality of separate spaced-apart dams fluid flows from said first channel into said second channel, and wherein said wall disposed between adjacent ones of said plurality of separate spaced-apart dams is operable to inhibit the flow of fluid from said first channel to said second channel between said spaced-apart zones; and
    a dilution channel for supplying a reagent, said dilution channel being bifurcated and intersecting with said first channel at two of said plurality of separate spaced-apart dams forming a first dilution intersection at the junction of said first channel and one of said bifurcated channels and a second dilution intersection at the junction of said first channel and another of said bifurcated channels for generating a concentration gradient of the reagent within said first channel whereby the reagent concentration varies in the direction of fluid flow in said first channel.

2. The apparatus as claimed in claim 1 wherein said first inlet for supplying a cell bearing fluid to said first channel is at a first liquid pressure, and wherein a second inlet is provided for supplying a fluid to said second channel at a second liquid pressure which is lower than the first liquid pressure.

3. The apparatus as claimed in claim 1 wherein said bifurcated dilution channels are perpendicular to said first channel at the intersection of said bifurcated dilution channels and said first channel.

4. The apparatus as claimed in claim 1 wherein said channels have a depth of about 18 microns.

5. The apparatus as claimed in claim 1 further comprising a cover disposed over said channels.

* * * * *